(12) United States Patent
Ball et al.

(10) Patent No.: US 11,686,730 B2
(45) Date of Patent: Jun. 27, 2023

(54) QUANTITATIVE ANTIBODY TEST

(71) Applicant: Quanterix Corporation, Billerica, MA (US)

(72) Inventors: Andrew Ball, Billerica, MA (US); Lei Chang, Billerica, MA (US); Syrena Fernandes, Billerica, MA (US); Joe Johnson, Billerica, MA (US); Jeremy Lambert, Billerica, MA (US); Dawn Mattoon, Billerica, MA (US); Tatiana Plavina, Billerica, MA (US); David Wilson, Billerica, MA (US)

(73) Assignee: Quanterix Corporation, Billerica, MA (US)

( * ) Notice: Subject to any disclaimer, the term of this patent is extended or adjusted under 35 U.S.C. 154(b) by 0 days.

(21) Appl. No.: 17/243,502

(22) Filed: Apr. 28, 2021

(65) Prior Publication Data
US 2021/0341479 A1    Nov. 4, 2021

Related U.S. Application Data

(60) Provisional application No. 63/053,364, filed on Jul. 17, 2020, provisional application No. 63/018,465, filed on Apr. 30, 2020.

(51) Int. Cl.
    *G01N 33/569* (2006.01)
    *G01N 33/567* (2006.01)

(52) U.S. Cl.
    CPC . *G01N 33/56983* (2013.01); *G01N 2333/165* (2013.01); *G01N 2469/20* (2013.01)

(58) Field of Classification Search
    CPC ......... G01N 2333/165; G01N 2469/20; G01N 33/56983
    See application file for complete search history.

(56) References Cited

U.S. PATENT DOCUMENTS

| | | | |
|---|---|---|---|
| 7,041,481 B2 | 5/2006 | Anderson et al. | |
| 7,129,091 B2 | 10/2006 | Ismagilov et al. | |
| 7,585,463 B2 | 9/2009 | Austin et al. | |
| 7,901,939 B2 | 3/2011 | Ismagliov et al. | |
| 8,020,571 B2 | 9/2011 | Honkanen et al. | |
| 8,222,047 B2 | 7/2012 | Duffy et al. | |
| 8,246,760 B2 | 8/2012 | Honkanen et al. | |
| 8,415,171 B2 | 4/2013 | Rissin et al. | |
| 8,592,221 B2 | 11/2013 | Fraden et al. | |
| 8,679,262 B2 | 3/2014 | Honkanen et al. | |
| 8,685,486 B2 | 4/2014 | Oliver et al. | |
| 8,811,704 B2 | 8/2014 | Honkanen et al. | |
| 8,846,415 B2 | 9/2014 | Duffy et al. | |
| 9,110,025 B2 | 8/2015 | Rissin et al. | |
| 9,527,085 B2 | 12/2016 | Austin et al. | |
| 9,551,663 B2 | 1/2017 | Rissin et al. | |
| 9,562,897 B2 | 2/2017 | Samuels et al. | |
| 9,678,068 B2 | 6/2017 | Duffy et al. | |
| 9,846,155 B2 | 12/2017 | Rissin et al. | |
| 9,896,717 B2 | 2/2018 | Hodges et al. | |
| 9,932,626 B2 | 4/2018 | Duffy et al. | |
| 9,952,237 B2 | 4/2018 | Fournier et al. | |
| 10,191,037 B2 | 1/2019 | Honkanen et al. | |
| 10,357,772 B2 | 7/2019 | Fraden et al. | |
| 10,533,998 B2 | 1/2020 | Link et al. | |
| 10,562,032 B2 | 2/2020 | Honkanen et al. | |
| 10,640,814 B2 | 5/2020 | Duffy et al. | |
| 10,675,626 B2 | 6/2020 | Fraden et al. | |
| 10,761,090 B2 | 9/2020 | Samuels et al. | |
| 10,960,397 B2 | 3/2021 | Fraden et al. | |
| 11,187,702 B2 | 11/2021 | Link et al. | |
| 2002/0143437 A1 | 10/2002 | Handique et al. | |
| 2002/0166582 A1 | 11/2002 | D'Connor et al. | |
| 2004/0072278 A1 | 4/2004 | Chou et al. | |
| 2005/0272159 A1 | 12/2005 | Ismagilov et al. | |
| 2006/0245978 A1 | 11/2006 | Prins | |
| 2007/0003442 A1 | 1/2007 | Link et al. | |
| 2007/0026439 A1 | 2/2007 | Faulstich et al. | |
| 2007/0077572 A1 | 4/2007 | Tawfik et al. | |
| 2007/0092898 A1* | 4/2007 | Hu ................... | G01N 33/56994 435/5 |
| 2007/0092914 A1 | 4/2007 | Griffiths et al. | |
| 2007/0184489 A1 | 8/2007 | Griffiths et al. | |
| 2008/0124726 A1 | 5/2008 | Monforte | |
| 2010/0075355 A1 | 3/2010 | Duffy et al. | |
| 2010/0075439 A1 | 3/2010 | Duffy et al. | |
| 2010/0075862 A1 | 3/2010 | Duffy et al. | |
| 2011/0212848 A1 | 9/2011 | Duffy et al. | |
| 2013/0142710 A1 | 6/2013 | Honkanen et al. | |

(Continued)

FOREIGN PATENT DOCUMENTS

WO    2007024914 A2    3/2007
WO    2019060607 A1    3/2019

OTHER PUBLICATIONS

Fatima Amanat, et al. Nat. Med. 2020, Jul. 26(7), pp. 1033-1036.*
Crawfold et al. medRxiv, published on Aug. 7, 2020.*
US Department of Health and Human Services. Biosafety in Micro-Biological and Biomedical Laboratories, 4th Ed., Washington, DC: US Government Printing Office, May 1999 (265 pages).
World Health Organization. Laboratory Biosafety Manual. Geneva: World Health Organization, 2004, 181 pages.
US Department of Health and Human Services. Biosafety in Micro-Biological and Biomedical Laboratories, 4th Ed., Washington, DC: US Government Printing Office, May 1999, pp. 1-10 (Table of Contents).

(Continued)

*Primary Examiner* — Bao Q Li
(74) *Attorney, Agent, or Firm* — Rimon PC

(57) ABSTRACT

The present disclosure relates to methods and compositions, e.g., kits, for quantitatively detecting an antibody of a subject to an infectious organism. In some embodiments, the present disclosure provides for methods and compositions, e.g., kits, for quantitatively detecting a human antibody to SARS-CoV-2 polypeptide or S (spike) polypeptide. Certain applications and uses of the present methods and compositions, e.g., kits, are also provided.

21 Claims, 16 Drawing Sheets
Specification includes a Sequence Listing.

(56) References Cited

U.S. PATENT DOCUMENTS

| | | |
|---|---|---|
| 2013/0266969 A1 | 10/2013 | Honkanen et al. |
| 2016/0123969 A1 | 5/2016 | Rissin et al. |
| 2018/0003703 A1 | 1/2018 | Duffy et al. |
| 2019/0094214 A1 | 3/2019 | Gildor et al. |
| 2019/0217289 A1 | 7/2019 | Chiu et al. |
| 2020/0070172 A1 | 3/2020 | Ismagilov et al. |
| 2020/0123592 A1 | 4/2020 | Díaz-Mochón et al. |
| 2021/0088519 A1 | 3/2021 | Link et al. |
| 2022/0050108 A1 | 2/2022 | Link et al. |

OTHER PUBLICATIONS

Clinical and Laboratory Standards Institute. Protection of Laboratory Workers from Occupationally Acquired Infections: Approved Guideline, 3rd Ed. CLSI Document M29-A3. Wayne, PA: Clinical and Laboratory Standards Institute, 2005, 11 pages.

Amanat, F., et al. "A Serological Assay to Detect SARS-CoV-2 Seroconversion in Humans". Nature Medicine, vol. 26, pp. 1033-1036 (2020). https://doi.org/10.1038/s41591-020-0913-5.

Azadeh, et al. "Calibration Curves in Quantitative Ligand Binding Assays: Recommendations and Best Practices for Preparation, Design, and Editing of Calibration Curves". AAPS J. 2017;20(1):22. Published Dec. 27, 2017. doi:10.1208/s12248-017-0159-4.

Findlay, et al. "Appropriate Calibration Curve Fitting in Ligand Binding Assays". AAPS J., 2007;9(2):E260-E267. Published Jun. 29, 2007. doi:10.1208/aapsj0902029.

Wilson, et al. "The Simoa HD-1 Analyzer: A Novel Fully Automated Digital Immunoassay Analyzer with Single-Molecule Sensitivity and Multiplexing". J Lab Autom. 2015, pp. 1-15. doi:10.1177/2211068215589580.

Korber, et al. bioRxiv preprint doi: https://doi.org/10.1101/2020.04.29.069054; posted May 5, 2020 (33 pages).

Rissin, D.M., et al. "Single-Molecule Enzyme-Linked Immunosorbent Assay Detects Serum Proteins at Subfemtomolar Concentrations". Nature Biotechnol., 2010;28:595-9.

Kan, et al. "Isolation and Detection of Single Molecules on Paramagnetic Beads using Sequential Fluid Flows in Microfabricated Polymer Array Assemblies". Lab Chip 2012;12:977-85.

"Immunity Passports" in the Context of COVID-19 https://www.who.int/news-room/commentaries/detail/immunity-passports-in-the-context-of-covid-19.

US Department of Health and Human Services. Biosafety in Micro-Biological and Biomedical Laboratories, 5th ed. Washington, DC: US Government Printing Office, 2007.

The First Preliminary Amendment in connection with U.S. Appl. No. 12/595,107.

Grimmer, et al., "Advanced Simulation of Droplet Microfluidics," 2018, arXiv:1810.01164 [physics.flu-dyn].

The Oct. 3, 2012 Office Action in connection with U.S. Appl. No. 12/595,107.

The Jan. 3, 2013 Amendment in connection with U.S. Appl. No. 12/595,107.

The May 15, 2013 Notice of Allowance in connection with U.S. Appl. No. 12/595,107.

The Apr. 10, 2019 Notice of Allowance in connection with U.S. Appl. No. 16/105,283.

The Jan. 18, 2019 Office Action in connection with U.S. Appl. No. 16/105,283.

Oxford American Dictionary and Thesaurus (2003) definitions of the words "each," "network," and "system".

Berthier and Silberzan, Microfluidics for Biotechnology, 1st ed. 2006 (excerpts), pp. xiii-xvi.

Oh et al., "Design of Pressure-Driven Microfluidic Networks using Electric Circuit Analogy," The Royal Society of Chemistry 2012, Lab Chip, DOI: 10.1039/c2tc20799k.

Hardt and Schönfeld, Microfluidic Technologies for Miniaturized Analysis Systems, 1st ed., 2007 (excerpts), pp. 1-8.

Berli, "Equivalent Circuit Modeling of Electrokinetically Driven Analytical Microsystems," Springer-Verlag 2007, Microfluid. Nanofluid., DOI: 10.1007/S10404-007-0191-2.

Wang et al., "System-Level Modeling and Simulation of Biochemical Assays in Lab-on-a-Chip Devices," Springer-Verlag 2006, Microfluid. Nanofluid., DOI: 10.1007/s10404-006-0123-6.

Shen, et al. "A Microduidic Chip Based Sequential Injection System with Trapped Droplet Liquid-Liquid Extraction and Chemiluminescence Detection". Lab Chip, 2006, 6, 1387-1389.

\* cited by examiner

Figure 1. Simoa HD-X Analyzer
(A) Major areas of the instrument.
(B) Overhead plan of the chemistry and digitization modules.

Matrix equivalency

Contrived samples consisting of negative, high negative, low positive, and high positive were prepared. Five matched sets of serum and plasma were spiked with endogenous SARS-CoV2-IgG from an IgG-positive serum sample. Samples were tested in duplicate in all matrices for each concentration, for a total of 40 results per matrix, and the results obtained from each matrix for each individual subject compared. The table shows positive percent agreement and negative percent agreement for plasma versus serum.

Sample preparation:

- A high positive sample was mixed with matched Serum / K2EDTA Plasma at 4 levels (according to table)
- Samples were further diluted to MRD and then tested to compare levels in each matrix

| | Serum (µg/ml) | Plasma (µg/ml) | % Bias | Serum (µg/ml) | Plasma (µg/ml) | % Bias |
|---|---|---|---|---|---|---|
| Donor 1 | 4.75 | 4.44 | -7.0% | 2.39 | 2.32 | -2.9% |
| Donor 2 | 4.46 | 4.73 | 5.6% | 2.23 | 2.38 | 3.9% |
| Donor 3 | 4.90 | 4.66 | -5.1% | 2.48 | 2.19 | -13.2% |
| Donor 4 | 4.52 | 4.67 | 3.2% | 2.34 | 2.38 | 1.4% |
| Donor 5 | 5.00 | 4.60 | -8.6% | 2.12 | 2.11 | -0.3% |
| | | Average | -2.4% | | Average | -2.2% |

| | Serum (µg/ml) | Plasma (µg/ml) | % Bias | Serum (µg/ml) | Plasma (µg/ml) | % Bias |
|---|---|---|---|---|---|---|
| Donor 1 | 0.33 | 0.33 | 0.6% | 0.04 | 0.00 | NaN |
| Donor 2 | 0.43 | 0.43 | 0.9% | 0.08 | 0.08 | 1.9% |
| Donor 3 | 0.40 | 0.31 | -27.7% | 0.02 | 0.03 | 41.6% |
| Donor 4 | 0.50 | 0.36 | -30.2% | 0.02 | 0.04 | 80.1% |
| Donor 5 | 0.46 | 0.44 | -4.7% | 0.14 | 0.08 | -72.5% |
| | | Average | -8.2% | | Average | 1.2% |
| | | | | | Grand Average | -3.7% |

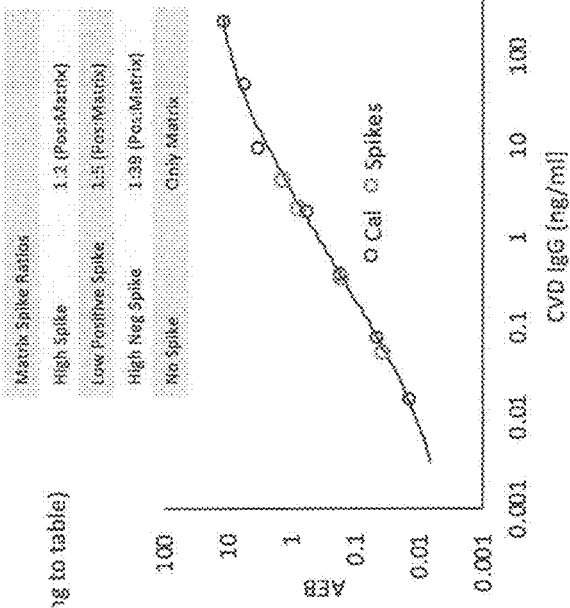

Matrix Spike Ratios:
| High Spike | 1:2 (Pos:Matrix) |
| Low Positive Spike | 1:5 (Pos:Matrix) |
| High Neg Spike | 1:39 (Pos:Matrix) |
| No Spike | Only Matrix |

Figure 6

Conclusion: Overall the Average Grand bias is -3.7% plasma to serum. The "No Spike" condition is impacted by higher variability due to being low in the assay range, below the Lower Limit of Quantification.

Parallelism between recombinant calibrator and endogenous target

Sample dilutions:
- A +ve serum and +ve K2 EDTA plasma were diluted in assay buffer to 1000x, and then serially 2-fold for a total of 8 dilutions
- Parallelism was demonstrated by comparing dilution corrected concentrations at each level to the initial dilution (1000x)
- Percent Recovery = (measured conc / expected conc); acceptable criteria are 100 ± 20% recovery average

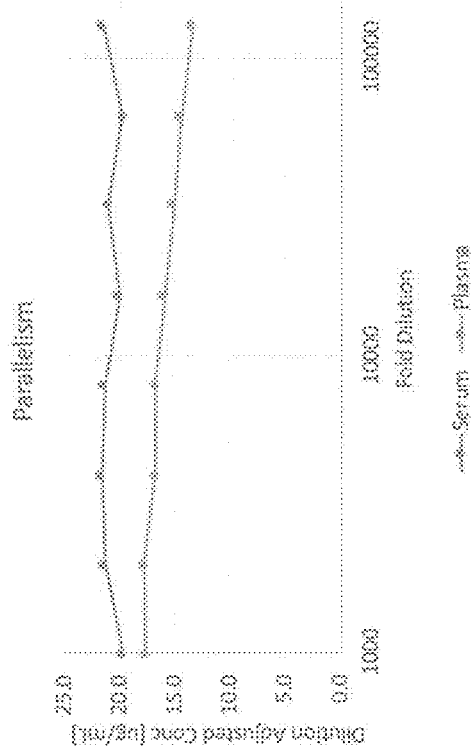

Figure 11

| Dilution | Serum conc [ng/ml] | Dil corr conc [ug/ml] | % Recovery | Plasma conc [ng/ml] | dil corr conc [ug/ml] | % Recovery |
|---|---|---|---|---|---|---|
| 1000x | 19.7 | 19.7 | 100% | 17.6 | 17.6 | 100% |
| 2000x | 10.7 | 21.4 | 108% | 8.9 | 17.8 | 101% |
| 4000x | 5.4 | 21.6 | 110% | 4.2 | 16.8 | 95% |
| 8000x | 2.7 | 21.4 | 109% | 2.1 | 16.8 | 95% |
| 16000x | 1.3 | 20.1 | 102% | 1.0 | 16.0 | 91% |
| 32000x | 0.66 | 21.1 | 107% | 0.47 | 15.1 | 86% |
| 64000x | 0.31 | 19.8 | 100% | 0.23 | 14.5 | 82% |
| 128000x | 0.17 | 21.6 | 110% | 0.11 | 13.5 | 76% |
|  | Ave | | 106% | | Ave | 91% |

Conclusion: Positive samples dilute linearly in assay buffer demonstrating: 1) parallelism between the recombinant calibrator and endogenous target being measured; 2) assay buffer is a good surrogate for sample matrix within the assay.

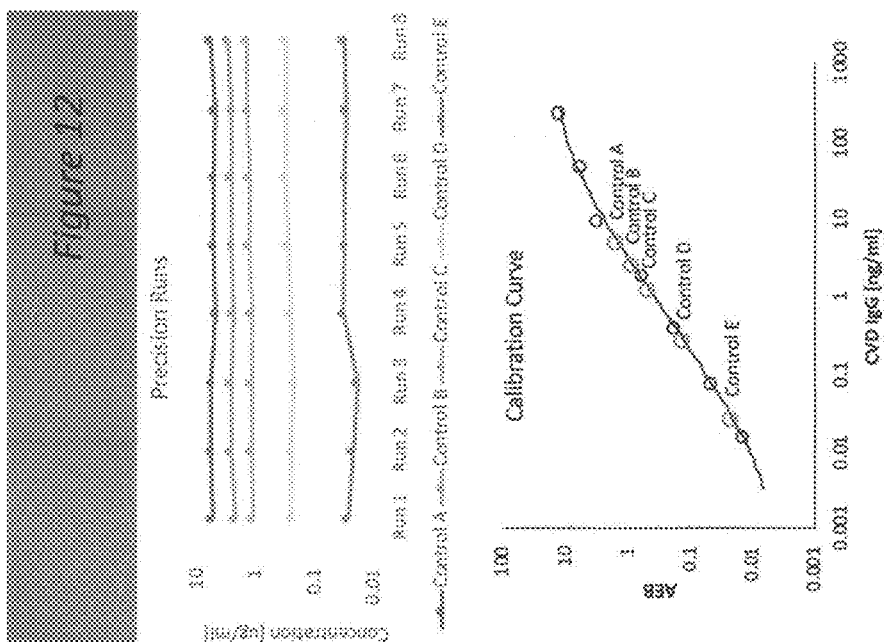

Interfering substances

Sample dilutions:
- A +ve Plasma positive pool were created by mixing 6 individuals. A negative pool was created by pooling 6 pre-pandemic samples
- Interferents were spiked into each pool at indicated concentrations
- Samples were measured at 1000X dilution.
- Percentage interference were calculated by ((Spiked sample/control sample)-1)X100%

| Interferent | Test Concentration | Prepandemic Plasma Pool | Positive Plasma Pool |
|---|---|---|---|
| Triglycerides | 1000 mg/dL | 15% | 14% |
| Hemolysate | 500 mg/dL | 6% | 21% |
| Bilirubin Conjugated | 20 mg/dL | 3% | 2% |
| Bilirubin Unconjugated | 20 mg/dL | -17% | 30% |
| RF | 30 U/mL | 30% | 30% |

*Figure 13*

QUANTITATIVE ANTIBODY TEST

The present application is a U.S. utility patent application, which claims priority to U.S. provisional patent application No. 63/018,465, filed on Apr. 30, 2020, and U.S. provisional patent application No. 63/053,364, filed on Jul. 17, 2020. The contents and disclosures of the above applications are incorporated herein by reference in their entireties for all purposes.

I. TECHNICAL FIELD

The present disclosure relates to methods and compositions, e.g., kits, for quantitatively detecting an antibody of a subject to an infectious organism. In some embodiments, the present disclosure provides for methods and compositions, e.g., kits, for quantitatively detecting a human antibody to SARS-CoV-2 polypeptide or S (spike) polypeptide. Certain applications and uses of the present methods and compositions, e.g., kits, are also provided.

II. SEQUENCE LISTING ON ASCII TEXT

This patent or application file contains a Sequence Listing submitted in computer readable ASCII text format (file name: 5239-2000100_SeqList_20210428_ST25.txt, date recorded: Apr. 28, 2021, size: 11,516 bytes). The content of the Sequence Listing file is incorporated herein by reference in its entirety.

III. BACKGROUND

Quanterix developed its single molecule array (Simoa) technology that makes it possible to count individual molecules in complex samples, such as blood, providing unprecedented sensitivity and precise quantitation of biomarkers. In 2010, Quanterix described this approach in a landmark publication in Nature Biotechnology where digitizing the signal in an enzyme-linked immunosorbent assay (ELISA) provided more than a 1000-fold improvement in the sensitivity of an assay for prostate specific antigen, allowing for detection of PSA in the serum of patients who had undergone radical prostatectomy and had previously undetectable PSA. Rissin D M, Kan C W, Campbell T G, et al. Single-molecule enzyme-linked immunosorbent assay detects serum proteins at subfemtomolar concentrations. Nat Biotech 2010; 28:595-99.

In January 2014, Quanterix launched the Simoa HD-1 Analyzer (2) and associated Simoa disk consumable (3) into the clinical research market. This instrument is a fully automated, sample-to-result system that provides on average a 1000-fold improvement in sensitivity for protein detection vs. conventional ELISA. More than 200 HD-1 systems have been installed worldwide, resulting in many hundreds of publications using Simoa. The technology has been adopted by almost all of the world's leading contract research organizations (CRO) that provide biomarker services for the pharmaceutical industry (such as Quintiles, Covance, and MyriadRBM), and the instrument is placed in nearly all of the top 25 pharmaceutical companies. Applications of Simoa have been focused on neurology, oncology, inflammatory diseases, and infectious diseases. Quanterix has developed a menu of more than 80 RUO assays for proteins in these areas, in both singleplex and multiplex formats. In 2019, Quanterix launched an updated version of its HD-1 platform. The new platform (HD-X) operates with the same principles and architecture as the HD-1 but includes hardware and software improvements to enhance reliability and usability. To-date, more than 70 HD-X instruments have been installed worldwide.

Simoa technology has been well described in the publications cited above (1-3). In brief, the technology involves performing a paramagnetic microbead-based sandwich ELISA, followed by isolation of individual capture beads in arrays of femtoliter-sized reaction wells. Singulation of capture beads within microwells permits buildup of fluorescent product from an enzyme label, so that signal from a single immunocomplex can be readily detected with a CCD camera. At very low analyte concentrations, Poisson statistics predict that bead-containing microwells in the array will contain either a single labeled analyte molecule or no analyte molecules, resulting in a digital signal of either "active" or "inactive" wells. Data collection involves counting active wells corresponding to single enzyme labels. At higher analyte concentrations, when all wells become occupied by at least one labeled analyte molecule, digital measurements transition to nondigital (analog) measurements of total fluorescence intensity. With single-molecule sensitivity, concentrations of labeling reagents can be lowered, resulting in reduced nonspecific background. This effect enables high signal-to-background ratios at extremely low analyte concentrations, enabling an average of 3-logs greater sensitivity than conventional ELISA methods.

The Quanterix COVID-19 IgG Antibody Test described in this submission is designed to performed by the Simoa HD-X Analyzer. The theory and operation of the HD-X instrument has been described in detail (2). In brief the instrument is a fully automated sequential cuvette processing robot for paramagnetic bead-based ELISA reagents. While commonly used IVD instrument architecture is utilized, the instrument is unique in that it incorporates Simoa technology for isolation and counting of single molecules. As an automated instrument, the robot pipettes sample directly from sample tubes and processes immunoassays and data reduction without user intervention. The HD-X is a high throughput lab system with placements throughout the US. We currently have an install base of approximately 50 instrument systems in or associated with CLIA labs around the country. Each instrument is capable of 2,000 sample results every 24 hours, representing a testing capability well over half a million tests/week nationally.

Additional and/or improved methods and kits for quantitatively detecting an antibody of a subject to an infectious organism are needed. The present disclosure provides for methods and kits to address this and the related needs.

IV. BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, the present disclosure provides for a method for quantitatively detecting an antibody of a subject to an infectious organism, which method comprises: a) contacting a sample from a subject with an antigen of an infectious organism, or a fragment or analog thereof, to allow binding between an antibody to said antigen of said infectious organism, if present in said sample, and said antigen of said infectious organism, or a fragment or analog thereof; b) assessing a detectable signal due to binding between said antibody and said antigen, or a fragment or analog thereof; and c) comparing said detectable signal to a calibration data set generated using a calibrator antibody that specifically binds to said antigen at multiple concentrations or levels to assess amount, concentration or level of said antibody in said sample. Any suitable calibrator antibody can be used in the present methods. In some embodiments, the calibrator antibody can be a chimeric antibody, or a fragment thereof, that comprises a constant region of a species of said subject and a variable region component or a variable region of a different species.

In another aspect, the present disclosure provides for a method for quantitatively detecting a human antibody to SARS-CoV-2 S (spike) polypeptide, which method comprises: a) contacting a sample from a subject with a SARS-CoV-2 S (spike) polypeptide, or a fragment or analog thereof, to allow binding between an antibody to a SARS-CoV-2 S (spike) polypeptide, if present in said sample, and said SARS-CoV-2 S (spike) polypeptide, or a fragment or analog thereof; b) assessing a detectable signal due to binding between said antibody and said SARS-CoV-2 S (spike) polypeptide, or a fragment or analog thereof; and c) comparing said detectable signal to a calibration data set generated using a calibrator antibody that specifically binds to said SARS-CoV-2 S (spike) polypeptide at multiple concentrations or levels to assess amount, concentration or level of said antibody in said sample. Any suitable calibrator antibody can be used in the present methods. In some embodiments, the calibrator antibody can be a chimeric antibody, or a fragment thereof, that comprises a human constant region and a variable region component or a variable region of a non-human species.

In still another aspect, the present disclosure provides for a kit for quantitatively detecting an antibody of a subject to an infectious organism, which kit comprises: a) an antigen of an infectious organism, or a fragment or analog thereof; and b) a calibrator antibody that specifically binds to said antigen for generating a calibration data set. Any suitable calibrator antibody can be used in the present kits. In some embodiments, the calibrator antibody can be a chimeric antibody, or a fragment thereof, that comprises a constant region of a species of said subject and a variable region component or a variable region of a different species.

In yet another aspect, the present disclosure provides for certain COVID-19 IgG Antibody Test, e.g., the Quanterix Simoa COVID-19 IgG Antibody Test. Both compositions, e.g., components, reagents, kits, systems, machines, and methods, e.g., methods of preparation and methods of using the certain COVID-19 IgG Antibody Test, are provided herein.

In some embodiments, the present disclosure relates to certain COVID-19 IgG Antibody Test, e.g., the Quanterix Simoa COVID-19 IgG Antibody Test, that is an automated paramagnetic microbead-based immunoassay intended for the quantitative detection of human IgG antibodies to SARS-CoV-2 in serum or plasma using the HD-X immunoassay system. The test measures IgG antibodies as indicative of an immune response to SARS-CoV-2 in patients suspected of previous SARS-CoV-2 infection, or for the detection of IgG seroconversion in patients following known recent SARS-CoV-2 exposure. The test is an aid in the diagnosis of patients suspected of prior or concomitant SARS-CoV-2 in conjunction with clinical presentation and the results of other laboratory tests. Generally, results from the Quanterix COVID-19 IgG Antibody Test should not be used as the sole basis for diagnosis and should not be used for the diagnosis of patients with acute SARS-CoV-2 infection.

In some embodiments, testing is limited to laboratories certified under the Clinical Laboratory Improvement Amendments of 1988 (CLIA), 42 U.S.C. § 263a, to perform moderate and high complexity tests.

In some embodiment, the Quanterix COVID-19 IgG Antibody Test is only for use under the Food and Drug Administration's Emergency Use Authorization. The test is for prescription use only and for in vitro diagnostic use only.

V. BRIEF DESCRIPTION OF THE DRAWINGS

Figure 3:
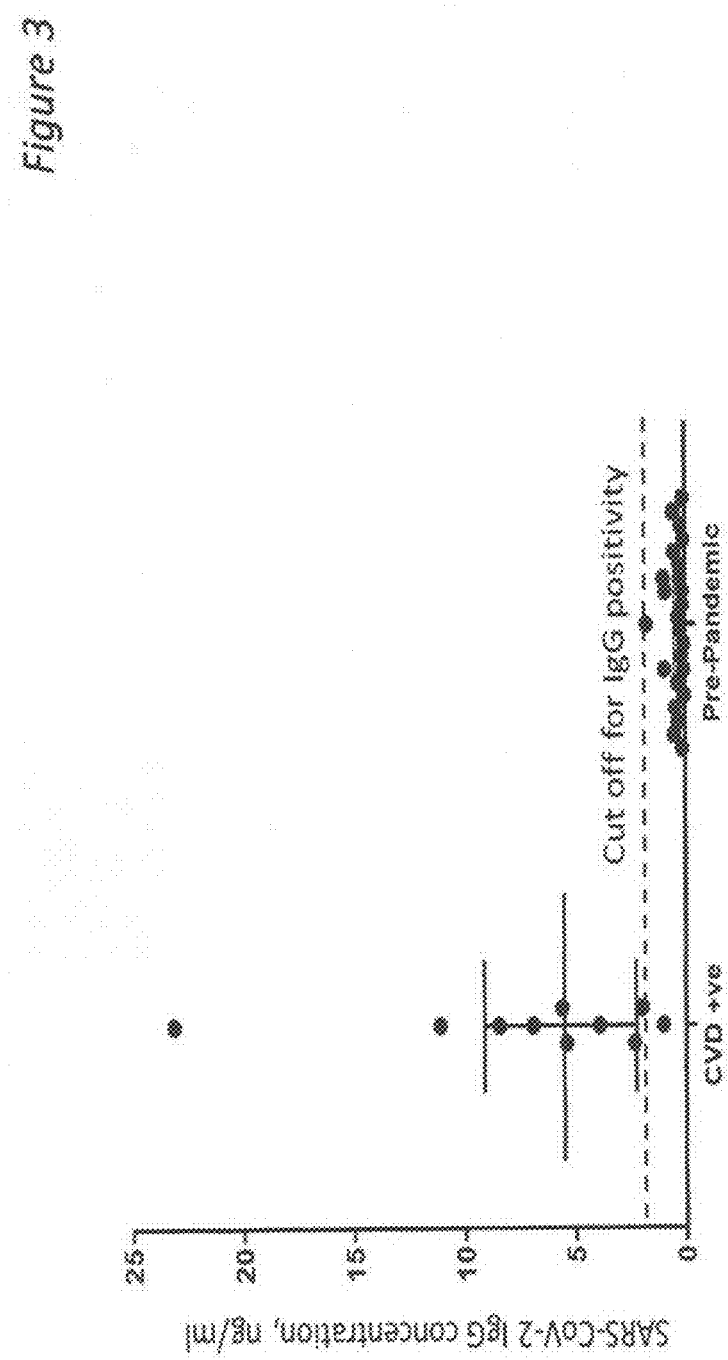

FIG. 3 illustrates exemplary SARS-CoV-2 IgG antibody concentrations for 25 pre-pandemic and 10 SARS-CoV-2 positive (based on RNA RT-PCR) serum samples. Specificity was 100%.

Figure 4:
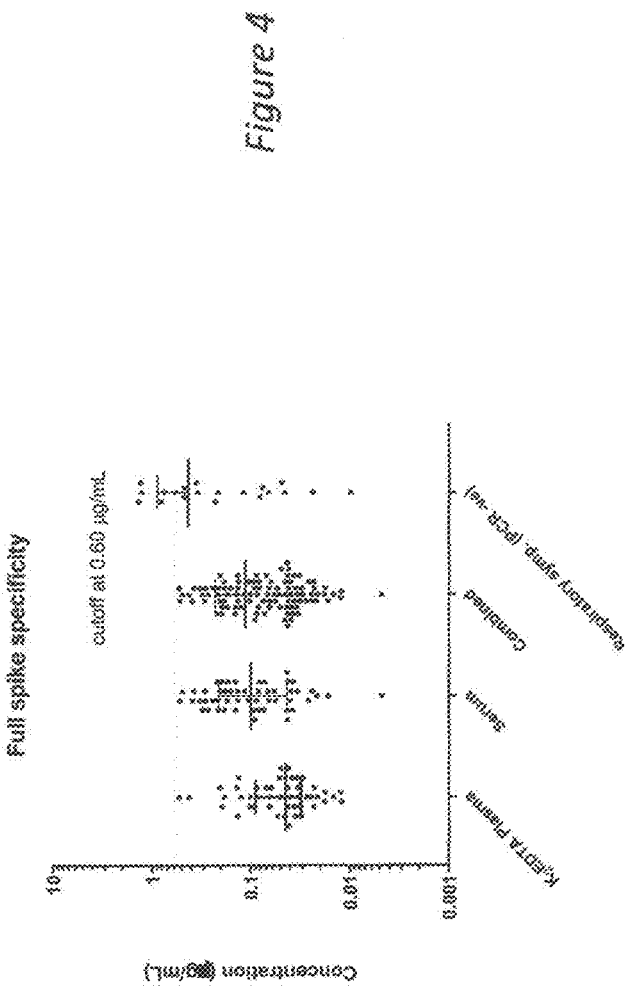

FIG. 4 illustrates exemplary cross-reactivity analysis.

Figure 5:
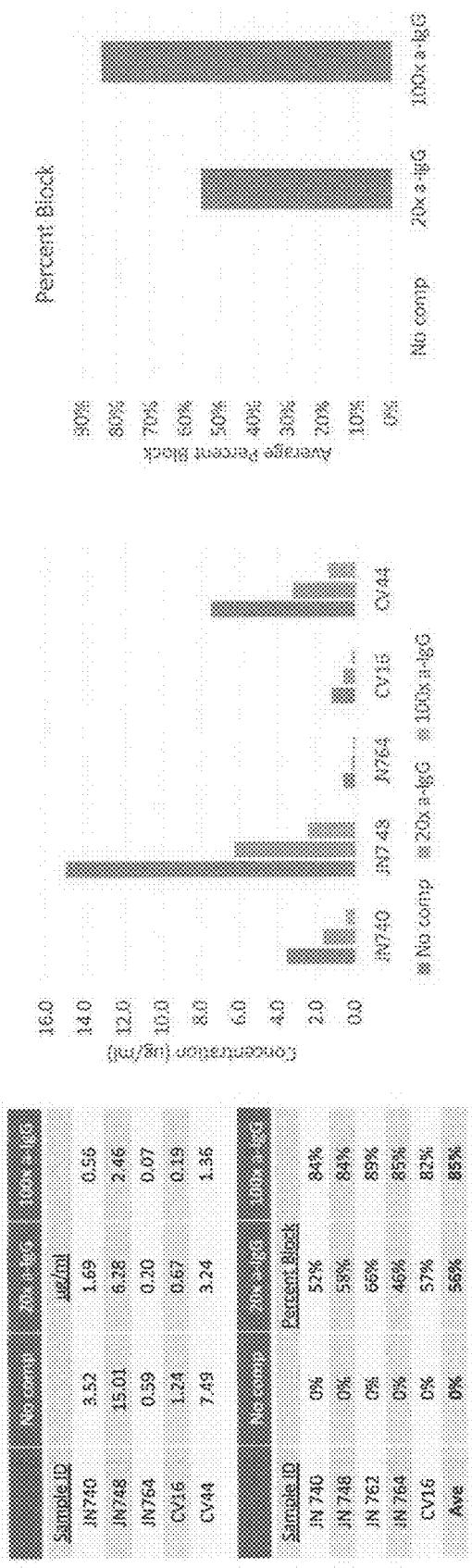

FIG. 5 illustrates exemplary IgG class analysis.

FIG. 6 illustrates exemplary matrix equivalency analysis.

Figure 7:
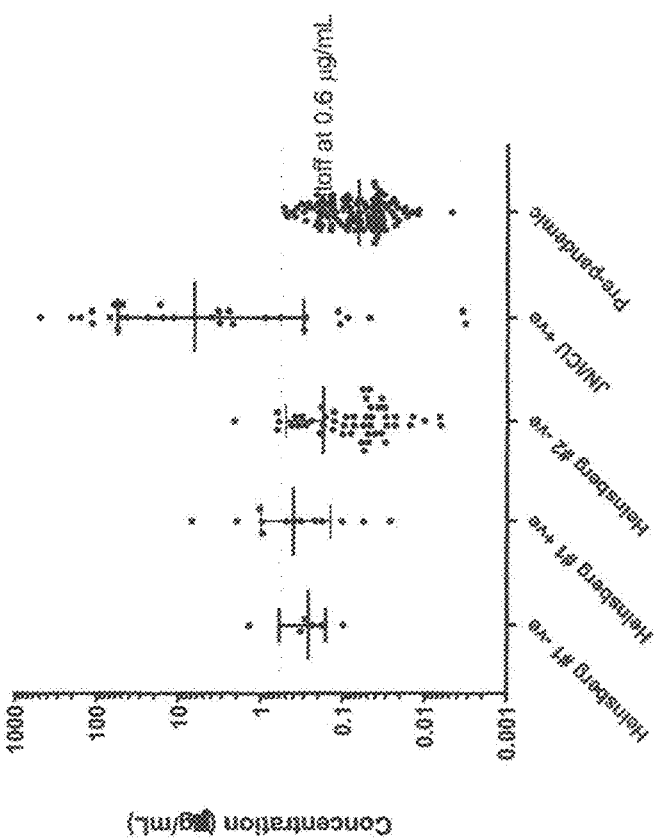

FIG. 7 illustrates exemplary clinical validity analysis.

Figure 8:
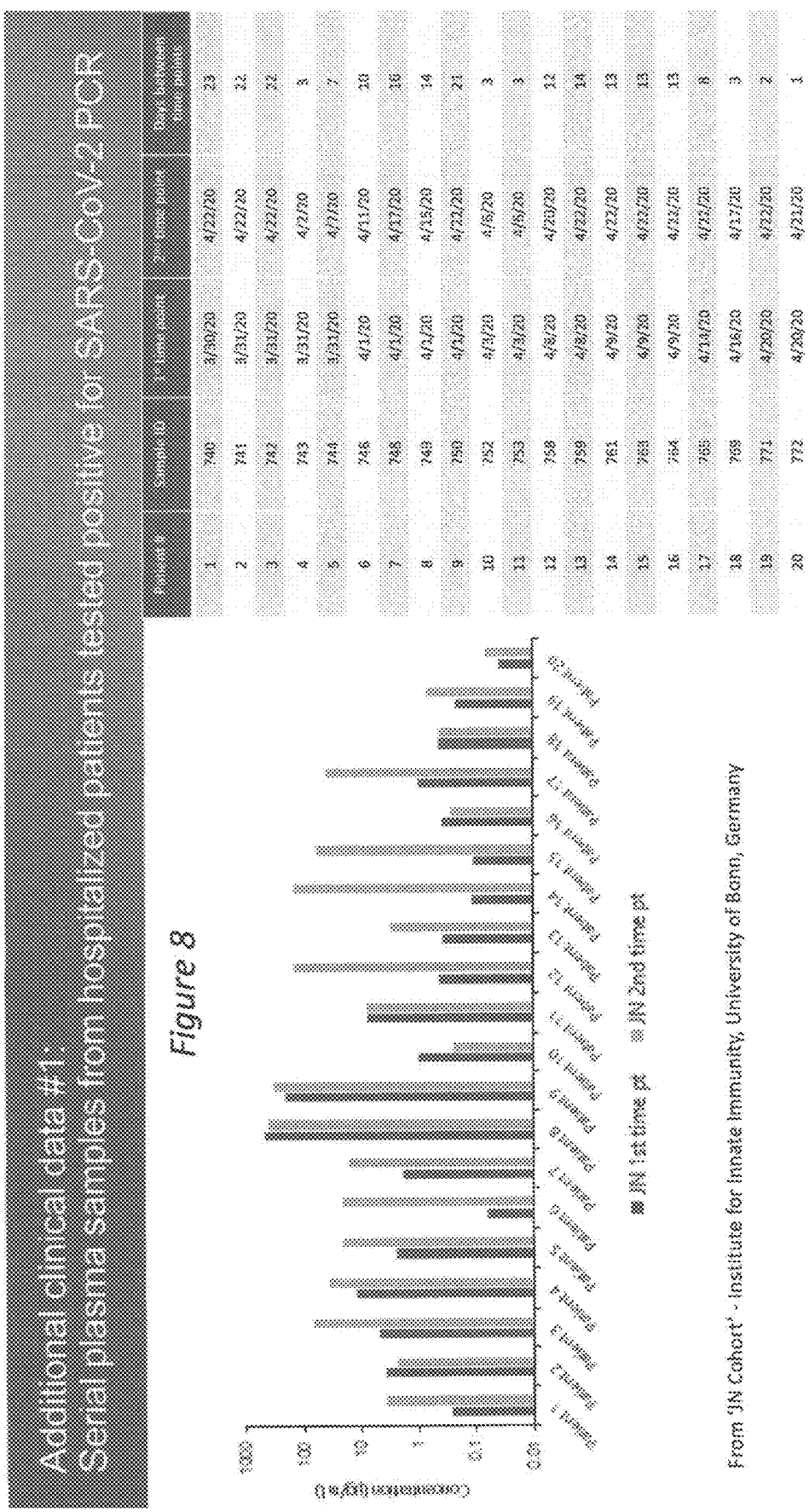

FIG. 8 illustrates exemplary additional clinical data #1.

Figure 9:
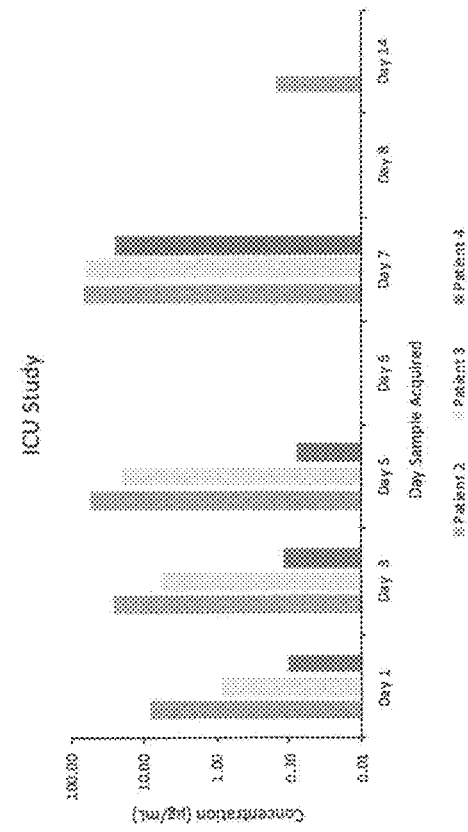

FIG. 9 illustrates exemplary additional clinical data #2.

Figure 10:
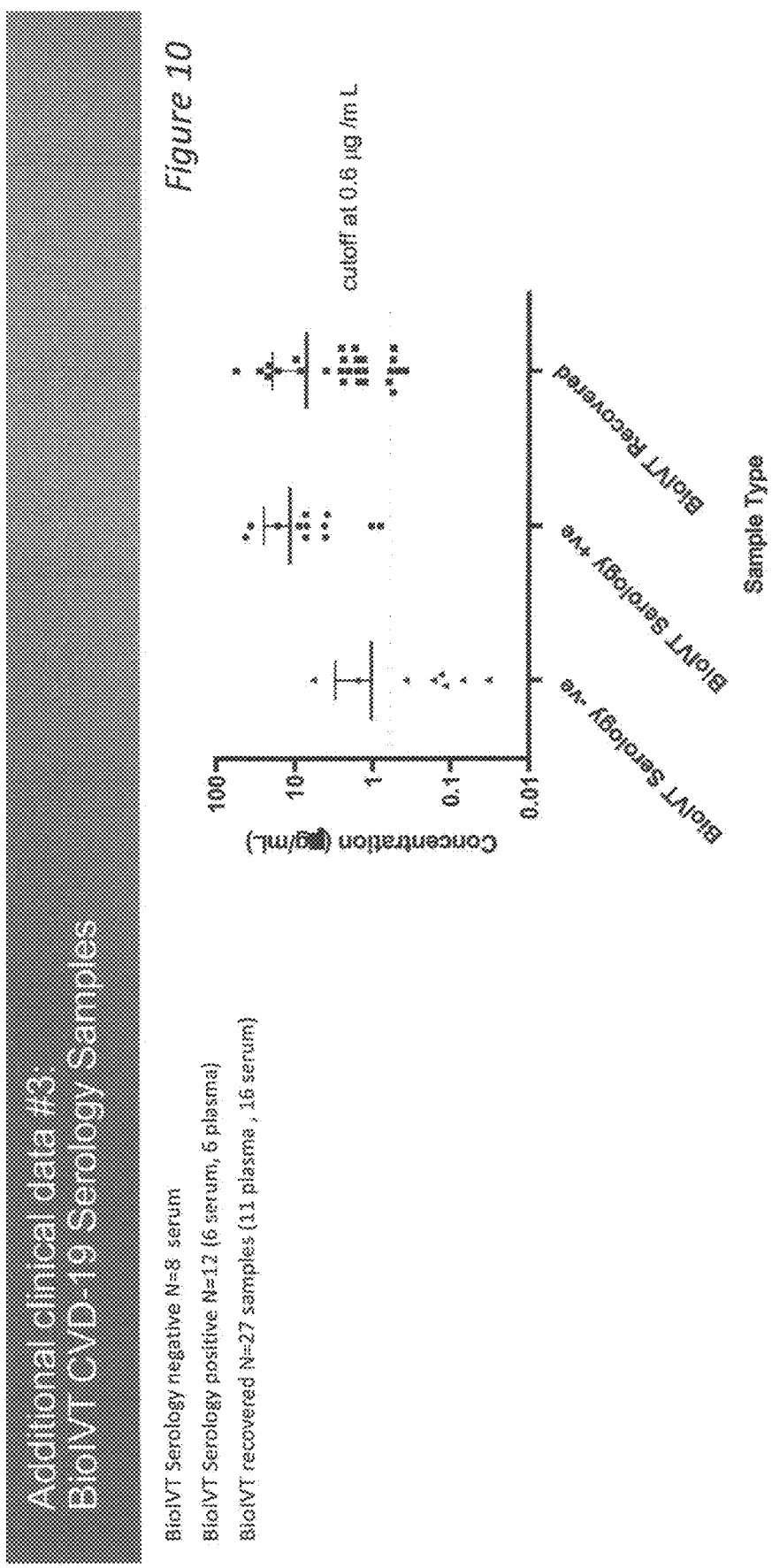

FIG. 10 illustrates exemplary additional clinical data #3.

FIG. 11 illustrates exemplary parallelism between recombinant calibrator and endogenous target.

FIG. 12 illustrates exemplary precision analysis.

FIG. 13 illustrates exemplary interfering substances analysis.

Figure 14:
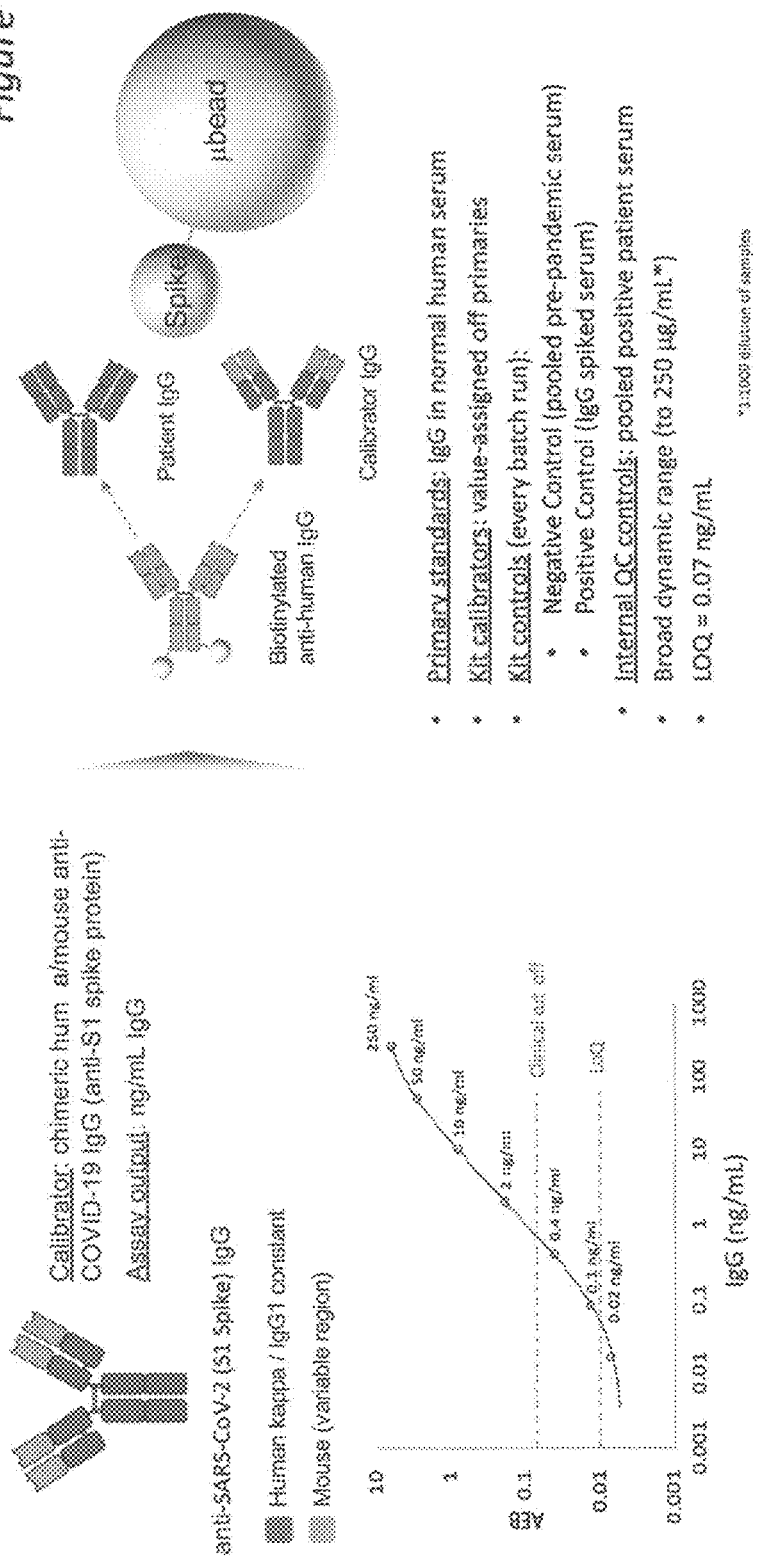

FIG. 14 illustrates exemplary quantification of IgG immune response.

Figure 15A:
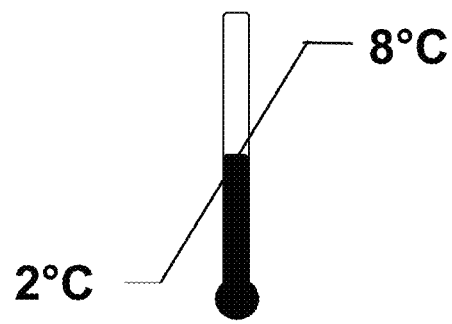
Figure 15B:
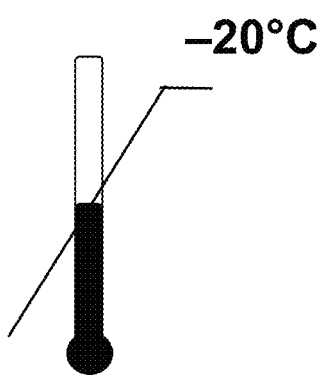

FIGS. 15 A-B graphically illustrates the temperature and positional requirements for storing the SARS-CoV-2 IgG Antibody Test reagents, calibrators and controls. FIG. 15A illustrates that the Simoa Quantitative SARS-CoV-2 IgG Antibody Test reagents must be stored at 2-8° C. in an upright position. FIG. 15B illustrates that the Simoa Quantitative SARS-CoV-2 IgG Antibody Test calibrators and controls must be stored at −80° C. and should be kept upright.

Figure 16:
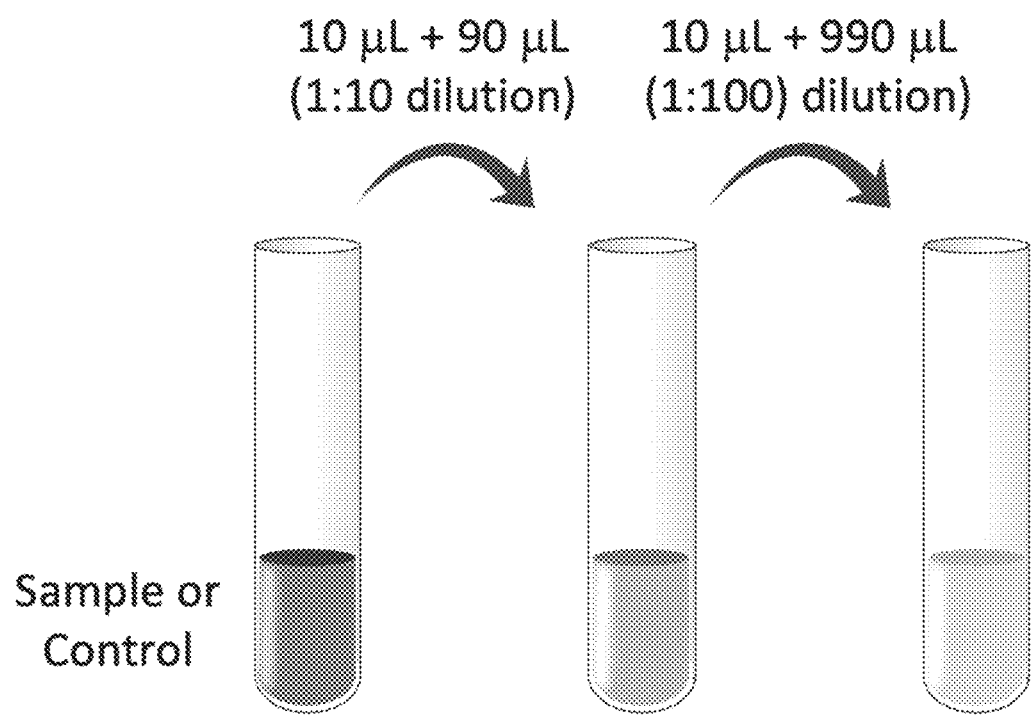

FIG. 16 illustrates how to perform a 2-step dilution.

VI. DETAILED DESCRIPTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, Gabriel, Stephens, Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Ausubel et al. eds., Current Protocols in Molecular Biology (1987); T. Brown ed., Essential Molecular Biology (1991), IRL Press; Goeddel ed., Gene Expression Technology (1991), Academic Press; A. Bothwell et al. eds., Methods for Cloning and Analysis of Eukaryotic Genes (1990), Bartlett Publ.; M. Kriegler, Gene Transfer and Expression (1990), Stockton Press; R. Wu et al. eds., Recombinant DNA Methodology (1989), Academic Press; M. McPherson et al., PCR: A Practical Approach (1991), IRL Press at Oxford University Press; Stryer, Biochemistry (4th Ed.) (1995), W. H. Freeman, New York N.Y.; Gait, Oligonucleotide Synthesis: A Practical Approach (2002), IRL Press, London; Nelson and Cox, Lehninger, Principles of Biochemistry (2000) 3rd Ed., W. H. Freeman Pub., New York, N.Y.; Berg, et al., Biochemistry (2002) 5th Ed., W. H. Freeman Pub., New York, N.Y.; D. Weir & C. Blackwell, eds., Handbook of Experimental Immunology (1996), Wiley-Blackwell; Cellular and Molecular Immunology (A. Abbas et al., W.B. Saunders Co. 1991, 1994); Current Protocols in Immunology (J. Coligan et al. eds. 1991), all of which are herein incorporated in their entireties by reference for all purposes.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

A. Definitions

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are not produced by enzyme digestion of a naturally-occurring intact antibody.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, the term "sample" refers to anything which may contain an analyte for which an analyte assay is desired. As used herein, a "sample" can be a solution, a suspension, liquid, powder, a paste, aqueous, non-aqueous or any combination thereof. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

B. Methods for Quantitatively Detecting an Antibody

In one aspect, the present disclosure provides for a method for quantitatively detecting an antibody of a subject to an infectious organism, which method comprises: a) contacting a sample from a subject with an antigen of an infectious organism, or a fragment or analog thereof, to allow binding between an antibody to said antigen of said infectious organism, if present in said sample, and said antigen of said infectious organism, or a fragment or analog thereof; b) assessing a detectable signal due to binding between said antibody and said antigen, or a fragment or analog thereof; and c) comparing said detectable signal to a calibration data set generated using a calibrator antibody that specifically binds to said antigen at multiple concentrations or levels to assess amount, concentration or level of said antibody in said sample, and optionally wherein said calibrator antibody is a chimeric antibody, or a fragment thereof, that comprises a constant region of a species of said subject and a variable region component or a variable region of a different species.

The present methods can be used for quantitatively detecting an antibody of a subject to an infectious organism in any suitable sample. For example, the present methods can be used for quantitatively detecting an antibody of a subject to an infectious organism in a urine, blood, dry blood spot, plasma, serum, saliva, semen, stool, sputum, cerebral spinal fluid, tear, mucus, and amniotic fluid sample. In some embodiments, the present methods can be used for quantitatively detecting an antibody of a subject to an infectious organism in a blood, plasma, serum, capillary blood, venous blood, or dried blood sample.

The present methods can be used for quantitatively detecting an antibody of any suitable subject to an infectious organism. For example, the present methods can be used for quantitatively detecting an antibody of a vertebrate or a mammal to an infectious organism. In some embodiments, the mammal is a human. In other embodiments, the mammal is a non-human mammal, e.g., a non-human primate such as a monkey, a rabbit, or a rodent.

Any suitable antigen of an infectious organism, or a fragment or analog thereof, can be used in the present methods. For example, the antigen can comprise a surface antigen or a non-surface antigen of an infectious organism, or a fragment or analog thereof. In another example, the antigen can comprise a polypeptide, lipid, sugar, polysaccharide, a fragment thereof, a combination thereof, of an infectious organism. In some embodiments, the surface antigen comprises a surface polypeptide, lipid, sugar, polysaccharide, a fragment thereof, a combination thereof, of an infectious organism.

In some embodiments, step a) of the present methods comprises contacting a sample from a subject with an intact or a whole antigen of an infectious organism. In some embodiments, step a) of the present methods comprises contacting a sample from a subject with a fragment or analog of an antigen of an infectious organism.

The present methods can be used for quantitatively detecting an antibody of a subject to any suitable infectious organism. For example, the present methods can be used for quantitatively detecting an antibody of a subject to a virus, a bacterium, a fungus or a parasite, e.g., a pathogenic virus, bacterium, fungus or parasite (See e.g., https://en.wikipedia.org/wiki/List_of_infectious_diseases).

In some embodiments, the present methods can be used for quantitatively detecting an antibody of a subject to a bacterium in a genus of *Bacillus, Bartonella, Bordetella, Borrelia, Brucella, Campylobacter, Chlamydia, Chlamydophila, Clostridium, Corynebacterium, Enterococcus, Escherichia*, e.g., *Escherichia coli, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio* or *Yersinia*. In some embodiments, the present methods can be used for quantitatively detecting an antibody of a subject to a fungus in a genus of *Candida, Aspergillus, Cryptococcus, Histoplasma*, e.g., *Histoplasma capsulatum, Pneumocystis*, or *Stachybotrys*, e.g., *Stachybotrys chartarum*. In some embodiments, the present methods can be used for quantitatively detecting an antibody of a subject to a parasite of a protozoa, a helminth or an ectoparasite. In some embodiments, the present methods can be used for quantitatively detecting an antibody of a subject to a virus that is Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echoviru, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Polyomavirus, Japanese encephalitis virus, Junin arenavirus, KI Polyomavirus, Polyomavirus, Kunjin virus, Lagos bat virus, Lyssavirus, Lake Victoria Marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Orthopoxvirus, Mumps virus, Murray valley encephalitis virus, New York virus, Nipah virus, Norwalk virus, onyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, Polyomavirus, West Nile virus, Yaba monkey tumor virus, Yaba-like disease virus, Yellow fever virus, or Zika virus.

The present methods can be used for quantitatively detecting an antibody of a subject to a DNA virus or a RNA virus. The present methods can be used for quantitatively detecting an antibody of a subject to a Coronavirus. The Coronavirus can be an alphacoronavirus, a betacoronavirus, a gammacoronavirus or a deltacoronavirus. The Coronavirus can be a human Coronavirus. In some embodiments, the present methods can be used for quantitatively detecting an antibody of a subject to human coronavirus OC43 (HCoV-OC43), human coronavirus HKU1 (HCoV-HKU1), human coronavirus 229E (HCoV-229E), human coronavirus NL63 (HCoV-NL63), middle east respiratory syndrome-related coronavirus (MERS-CoV), severe acute respiratory syndrome coronavirus (SARS-CoV or SARS-CoV-1) or severe acute respiratory syndrome coronavirus 2 (SARS-CoV-2). In some embodiments, the present methods can be used for quantitatively detecting an antibody of a subject to severe acute respiratory syndrome coronavirus 2 (SARS-CoV-2).

In the present methods for quantitatively detecting an antibody of a subject to a virus, any suitable viral antigen, or a fragment or analog thereof, can be used. For example, the viral antigen can comprise a viral surface antigen or a non-surface antigen. In another example, the viral antigen can comprise a polypeptide, lipid, sugar, polysaccharide, a fragment thereof, a combination thereof, of a virus. In some embodiments, the viral surface antigen can comprise a surface polypeptide, lipid, sugar, polysaccharide, a fragment thereof, a combination thereof, of a virus. In some embodiments, step a) of the present methods comprises contacting a sample from a subject with an intact or a whole viral antigen. In some embodiments, step a) of the present methods comprises contacting a sample from a subject with a fragment or analog of a viral antigen.

In the present methods for quantitatively detecting an antibody of a subject to a severe acute respiratory syndrome coronavirus 2 (BARS-CoV-2), any suitable SARS-CoV-2 antigen, or a fragment or analog thereof, can be used. For example, the antigen can comprise a polypeptide, lipid, sugar, polysaccharide, a fragment thereof, a combination thereof, of SARS-CoV-2. In some embodiments, the antigen can comprise a surface polypeptide, lipid, sugar, polysaccharide, a fragment thereof, a combination thereof, of SARS-CoV-2. Any suitable SARS-CoV-2 polypeptide, or a fragment or analog thereof, can be used in the present methods. For example, the SARS-CoV-2 S (spike) polypeptide, E (envelope) polypeptide, M (membrane) polypeptide, N (nucleocapsid) polypeptide, or a fragment or analog thereof, can be used in the present methods.

In some embodiments, step a) of the present methods comprises contacting a sample from a subject with an intact or a whole antigen of SARS-CoV-2. In some embodiments, step a) of the present methods comprises contacting a sample from a subject with a fragment or analog of an antigen of SARS-CoV-2.

Any suitable SARS-CoV-2 S (spike) polypeptide, or a fragment or analog thereof, can be used in the present methods. In some embodiments, step a) of the present methods comprises contacting a sample from a subject with an intact or a whole antigen of SARS-CoV-2 S (spike) polypeptide. In some embodiments, step a) of the present methods comprises contacting a sample from a subject with a fragment or analog of SARS-CoV-2 S (spike) polypeptide.

Any suitable fragment or analog of SARS-CoV-2 S (spike) polypeptide can be used in the present methods. For example, the fragment or analog of SARS-CoV-2 S (spike) polypeptide used in the present methods can comprise the extracellular domain or fragment of SARS-CoV-2 S (spike) polypeptide. In some embodiments, a SARS-CoV-2 S (spike) fragment comprising an amino acid sequence set forth in SEQ ID NO:1 ([PRO_0000449646; Aa 13-1273; GenBank Accession No. P0DTC2]), or the soluble trimeric version of the SARS-CoV-2 spike protein (e.g., the spike protein of SARS-CoV-2 187 isolate (GenBank: MN908947.3) (see e.g., medRxiv preprint doi: https://doi.org/10.1101/2020.03.17.20037713, version posted Mar. 18, 2020; and Vector pCAGGS Containing the SARS-Related Coronavirus 2, Wuhan-Hu-1 Spike Glycoprotein Gene." The following reagent was deposited by the Centers for Disease Control and Prevention and obtained through BEI Resources, NIAID, NIH: SARS-Related Coronavirus 2, Isolate USA-WA1/2020, NR-52281." (See e.g., Amanat, F., Stadlbauer, D., Strohmeier, S. et al. A serological assay to detect SARS-CoV-2 seroconversion in humans. Nat Med (2020). https://doi.org/10.1038/s41591-020-0913-5.)

```
>sp|P0DTC2|13-1273
SEQ ID NO: 1:
SQCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLDS

KTQSLLIVNNATNVVIKVCEFQFCNDPFLGVYYHKNNKSWMESEFRVYSS

ANNCTFEYVSQPFLMDLEGKQGNFKNLREFVFKNIDGYFKIYSKHTPINL

VRDLPQGFSALEPLVDLPIGINITRFQTLLALHRSYLTPGDSSSGWTAGA

AAYYVGYLQPRTFLLKYNENGTITDAVDCALDPLSETKCTLKSFTVEKGI

YQTSNFRVQPTESIVRFPNITNLCPFGEVFNATRFASVYAWNRKRISNCV

ADYSVLYNSASFSTFKCYGVSPTKLNDLCFTNVYADSFVIRGDEVRQIAP

GQTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVVV

LSFELLHAPATVCGPKKSTNLVKNKCVNFNFNGLTGTGVLTESNKKFLPF

QQFGRDIADTTDAVRDPQTLEILDITPCSFGGVSVITPGTNTSNQVAVLY

QDVNCTEVPVAIHADQLTPTWRVYSTGSNVFQTRAGCLIGAEHVNNSYEC

DIPIGAGICASYQTQTNSPRRARSVASQSIIAYTMSLGAENSVAYSNNSI

AIPTNFTISVTTEILPVSMTKTSVDCTMYICGDSTECSNLLLQYGSFCTQ

LNRALTGIAVEQDKNTQEVFAQVKQIYKTPPIKDFGGFNFSQILPDPSKP

SKRSFIEDLLFNKVTLADAGFIKQYGDCLGDIAARDLICAQKFNGLTVLP

PLLTDEMIAQYTSALLAGTITSGWTFGAGAALQIPFAMQMAYRFNGIGVT

QNVLYENQKLIANQFNSAIGKIQDSLSSTASALGKLQDVVNQNAQALNTL

VKQLSSNFGAISSVLNDILSRLDKVEAEVQIDRLITGRLQSLQTYVTQQL

IRAAEIRASANLAATKMSECVLGQSKRVDFCGKGYHLMSFPQSAPHGVVF

LHVTYVPAQEKNFTTAPAICHDGKAHFPREGVFVSNGTHWFVTQRNFYEP

QIITTDNTFVSGNCDVVIGIVNNTVYDPLQPELDSFKEELDKYFKNHTSP

DVDLGDISGINASVVNIQKEIDRLNEVAKNLNESLIDLQELGKYEQYIKW

PWYIWLGFIAGLIAIVMVTIMLCCMTSCCSCLKGCCSCGSCCKFDEDDSE

PVLKGVKLHYT
```

The present methods can use any suitable assay format. In some embodiments, step b) of the present methods comprises contacting a first complex formed between an antibody of a subject and an antigen of an infectious organism, or a fragment or analog thereof, with a binder that binds to the antibody in the first complex, and the binder comprising a detectable label, to form a second complex comprising the antibody, the antigen or a fragment or analog thereof, and the binder comprising the detectable label. Any suitable binder can be used. For example, the binder can be a protein or polypeptide binder, e.g., an antibody, or a non-protein binder, e.g., a binder comprising a peptide or nucleic acid scaffold, such as an aptamer.

In some embodiments, step b) of the present methods comprises 1) contacting a first complex formed between an antibody of a subject and an antigen of an infectious organism, or a fragment or analog thereof, with a binder that binds to the antibody in the first complex, and the binder comprising a first member of a binding pair, to form a second complex comprising the antibody, the antigen or a fragment or analog thereof, and the binder comprising the first member; and 2) contacting the second complex with a second member of the binding pair that comprises a detectable label and binds to the first member of the binding pair to form a third complex comprising the antibody, the antigen or a fragment or analog thereof, the binder comprising the first member of the binding pair, and the second member of the binding pair comprising a detectable label. Any suitable binder pair can be used. For example, the binding pair can comprise an antigen-antibody binding pair, an avidin (streptavidin)/biotin binding pair, a peptide-binder pair, or a DNA-binder pair.

The present methods can use any suitable detectable label. For example, the present methods can use a colorimetric, radioactive, enzymatic, luminescent or fluorescent label. In some embodiments, the present methods uses a fluorescent label.

The present methods can further comprise: 1) applying the second complex comprising the antigen or a fragment or analog thereof, the antibody, and the binder comprising a detectable label; or 2) applying the third complex comprising the antigen or a fragment or analog thereof, the antibody, the binder comprising the first member of the binding pair, and the second member of the binding pair comprising a detectable label, to a surface. The second complex or the third complex can be applied to any suitable surface. For example, the second complex or the third complex can be applied to a solid surface, a planar surface or a porous surface, or a microtiter plate, e.g., a 96/384 well microtiter plate, a microtiter plate comprising microwells, a microfluidic device. In some embodiments, the second complex or the third complex can be applied to a microfluidic device comprising an array of femtoliter reaction wells and to petition a single second complex or a single third complex in a femtoliter reaction well. The present methods can further comprise assessing a detectable signal from a single second complex or a single third complex in a femtoliter reaction well.

The second complex or third complex can be formed in any suitable manner. For example, the second complex or third complex can be formed on a particle, e.g., a bead. Any suitable particle(s) can be used. In some embodiments, the second complex or the third complex can be formed on a magnetic particle, a nanoparticle, or a polystyrene particle.

In some embodiments, the second complexes or third complexes are immobilized on particles and the particles are applied to a surface. The second complexes or the third complexes immobilized on particles can be applied to any suitable surface. For example, the second complexes or the third complexes immobilized on particles can be applied to a solid surface, a planar surface or a porous surface, or a microtiter plate, e.g., a 96/384 well microtiter plate, a microtiter plate comprising microwells, a microfluidic device. In some embodiments, the second complexes or the third complexes immobilized on particles can be applied to a microfluidic device comprising an array of femtoliter reaction wells and to petition a single second complex or a single third complex in a femtoliter reaction well. The present methods can further comprise assessing a detectable signal from a single second complex or a single third complex in a femtoliter reaction well.

The present methods can be conducted in an automated and/or digital assay. For example, the present methods can be conducted in an automated digital assay. In some embodiments, the present methods can be conducted using a fully automated digital immunoassay analyzer, e.g., the Simoa HD-1 Analyzer (See e.g., Wilson et al., Journal of Laboratory Automation, 1-15, © 2015 Society for Laboratory Automation and Screening, DOI: 10.1177/2211068215589580.) In some embodiments, the present methods can be conducted using instruments disclosed and/or claimed in U.S. Pat. Nos. 8,222,047, 8,846,415, 9,678,068, 8,415,171, 9,551,663, 9,952,237, 9,110,025, 9,846,155, 9,932,626, 10,640,814, 10,562,032, 10,191,037, 8,020,571, 8,246,760, 8,679,262, 8,685,486, 8,811,704, 7,585,463, 9,527,085; U.S. patent application publication Nos. US-2010-0075862-A1, US-2010-0075439-A1, US-2010-0075355-A1, US-2011-0212848-A1, US-2016-0123969-A1, US-2018-0003703-A1, US-2020-0123592, US-2013-0142710-A1, US-2013-0266969-A1; and PCT patent application publication No. WO2019/060607.

In some embodiments, an antigen of an infectious organism, or a fragment or analog thereof, is immobilized on a surface to allow binding between the antibody to the antigen of the infectious organism, if present in the sample, and the antigen of the infectious organism, or a fragment or analog thereof, to form a complex between the antibody and the antigen, or a fragment or analog thereof, on the surface. Any suitable surface can be used. For example, the surface can be part of a solid surface, a planar surface or a porous surface, or a microtiter plate, e.g., a 96/384 well microtiter plate, a microtiter plate comprising microwells, a microfluidic device, or a microfluidic device comprising an array of femtoliter reaction wells. In some embodiments, the present methods can be conducted in an ELISA format.

The calibration data set can be used in any suitable form. For example, the calibration data set can be used in a form of a calibration table or curve. A calibration table or curve can be obtained using any suitable procedure, process or algorithm. In some embodiments, a calibration curve is obtained using a curve fitting algorithm, e.g., 4-parameter logistical regression fitting algorithm. (See e.g., Azadeh et al., Calibration Curves in Quantitative Ligand Binding Assays: Recommendations and Best Practices for Preparation, Design, and Editing of Calibration Curves. *AAPS J.* 2017; 20(1):22. Published 2017 Dec. 27, doi:10.1208/s12218-017-0159-4; Findlay et al., Appropriate calibration curve fitting in ligand binding assays. *AAPS J.* 2007; 9(2):E260-E267. Published 2007 Jun. 29. doi:10.1208/aapsj0902029; and Wilson et al., The Simoa HD-1 Analyzer: A Novel Fully Automated Digital Immunoassay Analyzer with Single-Molecule Sensitivity and Multiplexing. *J. Lab Autom.* 2016; 21(4):533-547. doi:10.1177/2211068215589580.)

The calibration data set can be generated using a single calibrator antibody, or using a plurality of calibrator antibodies. The calibration data set can be generated using a calibrator antibody (or a plurality of calibrator antibodies) at any suitable concentrations or levels. In some embodiments, the calibration data set can be generated using a calibrator antibody (or a plurality of calibrator antibodies) at concentrations or levels ranging from about 0.001 ng/mL to about 10,000 ng/mL, e.g., at about 0.001 ng/mL, 0.01 ng/mL, 0.1 ng/mL, 1 ng/mL, 10 ng/mL, 100 ng/mL, 1,000 ng/mL, 10,0000 ng/mL, or any subrange thereof.

Any suitable calibrator antibody can be used in the present methods. For example, the calibrator antibody can comprise an intact antibody, e.g., an intact chimeric antibody. In another example, the antibody can be a recombinant, e.g., a recombinant chimeric antibody, or a fragment thereof. In some embodiments, the present methods can be used to quantitatively detect a human antibody to an infectious organism, and the calibrator antibody, or a fragment thereof, can comprise a constant region of a human antibody. In some embodiments, the present methods can be used to quantitatively detect a human antibody to an infectious organism, and the calibrator antibody can comprise a fully human antibody, a humanized antibody, a humanized chimeric antibody, or a fragment thereof.

In some embodiments, the calibrator antibody, or a fragment thereof, can comprise a variable region component or a variable region of a human, mouse, rat, rabbit, goat, pig, chicken, alpaca, donkey, sheep, hamster, Armenian hamster, golden Syrian hamster, guinea pig, cow, horse, llama, dog, cat, monkey, turkey, duck, recombinant, or mixed species antibody. In some embodiments, the calibrator antibody can comprise a monoclonal antibody, or a fragment thereof.

The present methods can be used to quantitatively detect any suitable class of antibody to an infectious organism. For example, the present methods can be used to detect a class of IgA, IgD, IgE, IgG, or IgM antibody to an infectious organism. In some embodiments, the present methods can be used to quantitatively detect a class of human IgA, IgD, IgE, IgG, or IgM antibody to an infectious organism. The present methods can be used to quantitatively detect a subclass (or isotype) of antibody to an infectious organism.

In some embodiments, the present methods can be used to quantitatively detect a class of IgA antibody to an infectious organism, and wherein the binder binds to the IgA antibody in the complex and the calibrator antibody is a chimeric IgA antibody. In some embodiments, the present methods can be used to quantitatively detect a class of IgD antibody to an infectious organism, and wherein the binder binds to the IgD antibody in the complex and the calibrator antibody is a chimeric IgD antibody. In some embodiments, the present methods can be used to quantitatively detect a class of IgE antibody to an infectious organism, and wherein the binder binds to the IgE antibody in the complex and the calibrator antibody is a chimeric IgE antibody. In some embodiments, the present methods can be used to quantitatively detect a class of IgG antibody to an infectious organism, and wherein the binder binds to the IgG antibody in the complex and the calibrator antibody is a chimeric antibody, e.g., a chimeric humanized mouse IgG antibody or a chimeric humanized mouse IgG specific for COVID-19 S1 spike protein. In some embodiments, the present methods can be used to quantitatively detect a class of IgM antibody to an infectious organism, and wherein the binder binds to the IgM antibody in the complex and the calibrator antibody is a chimeric IgM antibody.

The present methods can be used to quantitatively detect any suitable number of antibody or to antibodies an infectious organism. In some embodiments, the present methods can be used to quantitatively detect a single antibody to an infectious organism. In some embodiments, the present methods can be used to quantitatively detect multiple antibodies to an infectious organism. In some embodiments, the present methods can be used to quantitatively detect multiple antibodies to a single infectious organism. In some embodiments, the present methods can be used to quantitatively detect multiple antibodies to multiple infectious organisms. In some embodiments, the present methods can be used to quantitatively detect multiple antibodies in the same class or subclasses (or isotypes).

In some embodiments, the present methods can be used to quantitatively detect multiple antibodies in different subclasses (or isotypes). In some embodiments, the present methods can be used to quantitatively detect multiple antibodies in different classes. In some embodiments, the present methods can be used to quantitatively detect multiple antibodies in different subclasses (or isotypes). In some embodiments, the present methods can further comprise assessing comparison, e.g., a ratio, between or among concentrations or levels of antibodies in different subclasses (or isotypes).

In some embodiments, the present methods can be used to quantitatively detect an antibody to SARS-CoV-2 in a human. In some embodiments, the present methods can be used to quantitatively detect an IgG antibody to SARS-CoV-2 in a human.

In some embodiments, the present methods can be used to quantitatively detect an antibody, e.g., an IgG antibody, to SARS-CoV-2 protein mutant(s) or variant(s) in a subject or a human. The SARS-CoV-2 protein mutant(s) or variant(s) include mutant(s) or variant(s) with amino acid addition(s), deletion(s) and/or substitution(s). In the methods for quantitatively detecting an antibody, e.g., an IgG antibody, to SARS-CoV-2 protein mutant(s) or variant(s), the corresponding SARS-CoV-2 protein mutant(s) or variant(s) can be used as an antigen, or a fragment thereof, to contact with an antibody in a subject or a human.

In some embodiments, the present methods can be used to quantitatively detect an antibody to SARS-CoV-2 spike (S) protein in a subject or a human. In some embodiments, the present methods can be used to quantitatively detect an IgG antibody to spike (S) protein in a subject or a human. In some embodiments, the present methods can be used to quantitatively detect an antibody, e.g., an IgG antibody, to SARS-CoV-2 spike (S) protein mutant(s) or variant(s) in a subject or a human. The SARS-CoV-2 protein spike (S) mutant(s) or variant(s) include mutant(s) or variant(s) with amino acid addition(s), deletion(s) and/or substitution(s). Exemplary spike (S) protein mutant(s) or variant(s) include D614G, L5F, L8V, V367F, G476S, V483A, H49Y, Y145H/del, Q239K, A831V, D839Y/N/E, P1263L, and/or a combination thereof (See e.g., bioRxiv preprint doi: https://doi.org/10.1101/2020.04.29.069054; posted May 5, 2020). In the methods for quantitatively detecting an antibody, e.g., an IgG antibody, to SARS-CoV-2 spike (S) protein mutant(s) or variant(s), the corresponding SARS-CoV-2 spike (S) protein mutant(s) or variant(s) can be used as an antigen, or a fragment thereof, to contact with an antibody in a subject or a human.

The present methods can be conducted or performed in any suitable format or manner. For example, the present methods can be conducted or performed manually, can be semi-automated or fully automated.

The present methods can be conducted or performed with any suitable throughput. For example, the present methods can have a throughput ranging from about 10 tests/hour to about 100 tests/hour, e.g., about 10 tests/hour, 20 tests/hour, 30 tests/hour, 40 tests/hour, 50 tests/hour, 60 tests/hour, 70 tests/hour, 80 tests/hour, 90 tests/hour, 100 tests/hour, or any subrange thereof.

The present methods can be conducted or performed in any suitable time period. For example, the present methods can be conducted in a time period from about 20 minutes to about 300 minutes, e.g., about 20 minutes, 30 minutes, 40 minutes, 50 minutes, 60 minutes, 70 minutes, 80 minutes, 90 minutes, 100 minutes, 150 minutes, 200 minutes, 250 minutes, 300 minutes, or any subrange thereof, till first result or results of a set number of tests, e.g., about 250-300 samples, are obtained.

In some embodiments, the present methods can be used for quantitatively detecting an antibody to COVID-19 S1 spike protein, e.g., a class of IgG antibody to COVID-19 S1 spike protein, and has a detection cut-off from about 2 ng/mL to about 5 ng/mL, e.g., about 2 ng/mL, 3 ng/mL, 4 ng/mL, 5 ng/mL, or any subrange thereof.

In some embodiments, the present methods can be used for quantitatively detecting an antibody to COVID-19 S1 spike protein, e.g., a class of IgG antibody to COVID-19 S1 spike protein, and have a precision (or CV) ranging from about 3% to about 30%, e.g., about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or any subrange thereof. In some embodiments, the present methods can have a between-run precision CV ranging from 5% to about 20%, e.g., about 5%, 6%, 7%, 8%, 9%, 10%, 11%, 12%, 13%, 14%, 15%, 16%, 17%, 18%, 19%, 20%, or any subrange thereof. In some embodiments, the present methods can have a within-run precision CV ranging from 3% to 30%, e.g., about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or any subrange thereof.

In some embodiments, the present methods can be used for quantitatively detecting an antibody to COVID-19 S1 spike protein, e.g., a class of IgG antibody to COVID-19 S1 spike protein, and can have a sensitivity ranging from about 2 fg/mL to about 1 ng/mL, e.g., about 2 fg/mL, 10 fg/mL, 100 fg/mL, 1,000 fg/mL, 1,000 fg/mL, 0.01 ng/mL, 0.1 ng/mL, 1 ng/mL, or any subrange thereof.

In some embodiments, the present methods can be used for quantitatively detecting an antibody to COVID-19 S1 spike protein, e.g., a class of IgG antibody to COVID-19 S1 spike protein, and can have a specificity, e.g., IgG specificity, ranging from about 70% to about 100%, e.g., about 70%, 75%, 80%, 85%, 90%, 95%, 96%, 97%, 98%, 99%, 100%, or any subrange thereof.

In some embodiments, the present methods can be used for quantitatively detecting an antibody to COVID-19 S1 spike protein, e.g., a class of IgG antibody to COVID-19 S1 spike protein, and the quantitation results from comparable serum and plasma samples are within from about 0% to about 20% of each other, e.g., about 0%, 1%, 2%, 3%, 4%, 5%, 6%, 7%, 8%, 9%, 10%, 11%, 12%, 13%, 14%, 15%, 16%, 17%, 18%, 19%, 20%, or any subrange thereof.

The present methods can be used for any suitable purposes or utilities. For example, the present methods can be used to aid or facilitate diagnosis, prognosis, risk assessment, stratification and/or treatment monitoring of infection by an infectious organism in a subject, and/or for research and drug/vaccine discovery and/or development.

The present methods can be used to assess an immune response to an infectious organism in a subject. For example, the present methods can be used to assess an immune response to SARS-CoV-2 in a subject, e.g., a human subject or patient.

The present methods can be used to assess past infection by an infectious organism in a subject. For example, the present methods can be used to assess past infection by SARS-CoV-2 in a subject, e.g., a human subject or patient.

The present methods can be used to assess IgG seroconversion to an infectious organism in a subject. For example, the present methods can be used to assess IgG seroconversion to SARS-CoV-2 in a subject, e.g., a human subject or patient.

In another aspect, the present disclosure provides for a method for quantitatively detecting a human antibody to SARS-CoV-2 S (spike) polypeptide, which method comprises: a) contacting a sample from a subject with a SARS-CoV-2 S (spike) polypeptide, or a fragment or analog thereof, to allow binding between an antibody to a SARS-CoV-2 S (spike) polypeptide, if present in said sample, and said SARS-CoV-2 S (spike) polypeptide, or a fragment or analog thereof; b) assessing a detectable signal due to binding between said antibody and said SARS-CoV-2 S (spike) polypeptide, or a fragment or analog thereof; and c) comparing said detectable signal to a calibration data set generated using a calibrator antibody that specifically binds to said SARS-CoV-2 S (spike) polypeptide at multiple concentrations or levels to assess amount, concentration or level of said antibody in said sample, and, wherein said calibrator antibody is a chimeric antibody, or a fragment thereof, that comprises a human constant region and a variable region component or a variable region of a non-human species.

C. Kits for Quantitatively Detecting an Antibody

In still another aspect, the present disclosure provides for a kit for quantitatively detecting an antibody of a subject to an infectious organism, which kit comprises: a) an antigen of an infectious organism, or a fragment or analog thereof; and b) a calibrator antibody that specifically binds to said antigen, optionally at multiple concentrations or levels, for generating a calibration data set.

The present kits can be used for quantitatively detecting an antibody of a subject to an infectious organism in any suitable sample. For example, the present kits can be used for quantitatively detecting an antibody of a subject to an infectious organism in a urine, blood, dry blood spot, plasma, serum, saliva, semen, stool, sputum, cerebral spinal fluid, tear, mucus, and amniotic fluid sample. In some embodiments, the present kits can be used for quantitatively detecting an antibody of a subject to an infectious organism in a blood, plasma, serum, capillary blood, venous blood, or dried blood sample.

The present kits can be used for quantitatively detecting an antibody of any suitable subject to an infectious organism. For example, the present kits can be used for quantitatively detecting an antibody of a vertebrate or a mammal to an infectious organism. In some embodiments, the mammal is a human. In other embodiments, the mammal is a non-human mammal, e.g., a non-human primate such as a monkey, a rabbit, or a rodent.

The present kits can comprise any suitable antigen of an infectious organism, or a fragment or analog thereof. For example, the antigen can comprise a surface antigen or a non-surface antigen of an infectious organism, or a fragment or analog thereof. In another example, the antigen can comprise a polypeptide, lipid, sugar, polysaccharide, a fragment thereof, a combination thereof, of an infectious organism. In some embodiments, the surface antigen comprises a surface polypeptide, lipid, sugar, polysaccharide, a fragment thereof, a combination thereof, of an infectious organism. In some embodiments, the present kits comprise an intact or a whole antigen. In some embodiments, the present kits comprise a fragment or analog of an antigen.

The present kits can be used for quantitatively detecting an antibody of a subject to any suitable infectious organism. For example, the present kits can be used for quantitatively detecting an antibody of a subject to a virus, a bacterium, a fungus or a parasite, e.g., a pathogenic virus, bacterium, fungus or parasite (See e.g., https://en.wikipedia.org/wiki/List_of_infectious_diseases).

In some embodiments, the present kits can be used for quantitatively detecting an antibody of a subject to a bacterium in a genus of *Bacillus, Bartonella, Bordetella, Bor-* relia, *Brucella, Campylobacter, Chlamydia, Chlamydophila, Clostridium, Corynebacterium, Enterococcus, Escherichia*, e.g., *Escherichia coli, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio* or *Yersinia*. In some embodiments, the present kits can be used for quantitatively detecting an antibody of a subject to a fungus in a genus of *Candida, Aspergillus, Cryptococcus, Histoplasma*, e.g., *Histoplasma capsulatum, Pneumocystis*, or *Stachybotrys*, e.g., *Stachybotrys chartarum*. In some embodiments, the present kits can be used for quantitatively detecting an antibody of a subject to a parasite of a protozoa, a helminth or an ectoparasite. In some embodiments, the present kits can be used for quantitatively detecting an antibody of a subject to a virus that is Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolaviru, Echoviru, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Polyomavirus, Japanese encephalitis virus, Junin arenavirus, KI Polyomavirus, Polyomavirus, Kunjin virus, Lagos bat virus, Lyssavirus, Lake Victoria Marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Orthopoxvirus, Mumps virus, Murray valley encephalitis virus, New York virus, Nipah virus, Norwalk virus, onyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, Polyomavirus, West Nile virus, Yaba monkey tumor virus, Yaba-like disease virus, Yellow fever virus, or Zika virus.

The present kits can be used for quantitatively detecting an antibody of a subject to a DNA virus or a RNA virus. The present kits can be used for quantitatively detecting an antibody of a subject to a Coronavirus. The Coronavirus can be an alphacoronavirus, a betacoronavirus, a gammacoronavirus or a deltacoronavirus. The Coronavirus can be a human Coronavirus. In some embodiments, the present kits can be used for quantitatively detecting an antibody of a subject to human coronavirus OC43 (HCoV-OC43), human coronavirus HKU1 (HCoV-HKU1), human coronavirus 229E (HCoV-229E), human coronavirus NL63 (HCoV-NL63), middle east respiratory syndrome-related coronavirus (MERS-CoV), severe acute respiratory syndrome coronavirus (SARS-CoV or SARS-CoV-1) or severe acute respiratory syndrome coronavirus 2 (SARS-CoV-2). In some embodiments, the present kits can be used for quantitatively detecting an antibody of a subject to severe acute respiratory syndrome coronavirus 2 (SARS-CoV-2).

In the present kits for quantitatively detecting an antibody of a subject to a virus, any suitable viral antigen, or a fragment or analog thereof, can be used. For example, the viral antigen can comprise a viral antigen or a non-surface antigen. In another example, the viral antigen can comprise a surface polypeptide, lipid, sugar, polysaccharide, a fragment thereof, a combination thereof, of a virus. In some embodiments, the viral surface antigen can comprise a surface polypeptide, lipid, sugar, polysaccharide, a fragment thereof, a combination thereof, of a virus. In some embodiments, the present kits comprise an intact or a whole viral antigen. In some embodiments, the present kits comprise a fragment or analog of a viral antigen.

In the present kits for quantitatively detecting an antibody of a subject to a severe acute respiratory syndrome coronavirus 2 (SARS-CoV-2), any suitable SARS-CoV-2 antigen, or a fragment or analog thereof, can be used. For example, the antigen can comprise a polypeptide, lipid, sugar, polysaccharide, a fragment thereof, a combination thereof, of SARS-CoV-2. In some embodiments, the antigen can comprise a surface polypeptide, lipid, sugar, polysaccharide, a fragment thereof, a combination thereof, of SARS-CoV-2. Any suitable SARS-CoV-2 polypeptide, or a fragment or analog thereof, can be used in the present kits. For example, the SARS-CoV-2 S (spike) polypeptide, E (envelope) polypeptide, M (membrane) polypeptide, N (nucleocapsid) polypeptide, or a fragment thereof, can be used in the present kits.

In some embodiments, the present kits comprise an intact or a whole antigen of SARS-CoV-2. In some embodiments, the present kits comprise a fragment or analog of an antigen of SARS-CoV-2.

Any suitable SARS-CoV-2 S (spike) polypeptide, or a fragment or analog thereof, can be used in the present kits. In some embodiments, the present kits comprise an intact or a whole antigen of SARS-CoV-2 S (spike) polypeptide. In some embodiments, the present kits comprise a fragment or analog of SARS-CoV-2 S (spike) polypeptide.

Any suitable fragment or analog of SARS-CoV-2 S (spike) polypeptide can be used in the present kits. For example, the fragment or analog of SARS-CoV-2 S (spike) polypeptide used in the present kits can comprise the extracellular domain or fragment of SARS-CoV-2 S (spike) polypeptide. In some embodiments, a SARS-CoV-2 S (spike) fragment comprises an amino acid sequence set forth in SEQ ID NO:1 ([PRO_0000449646; Aa 13-1273; GenBank Accession No. P0DTC2]), or the soluble trimeric version of the SARS-CoV-2 spike protein (e.g., the spike protein of SARS-CoV-2 187 isolate (GenBank: MN908947.3) (see e.g., medRxiv preprint doi: https://doi.org/10.1101/2020.03.17.20037713, version posted Mar. 18, 2020; and Vector pCAGGS Containing the SARS-Related Coronavirus 2, Wuhan-Hu-1 Spike Glycoprotein Gene." The following reagent was deposited by the Centers for Disease Control and Prevention and obtained through BEI Resources, NIAID, NIH: SARS-Related Coronavirus 2, Isolate USA-WA1/2020, NR-52281. (See e.g., Amanat, F., Stadlbauer, D., Strohmeier, S. et al. A serological assay to detect SARS-CoV-2 seroconversion in humans. *Nat Med* (2020). https://doi.org/10.1038/s41591-020-0913-5).)

>sp|P0DTC2|13-1273
SEQ ID NO: 1:
SQCVNLTTRTQLPPAYTNSFTRGVYYPDKVFRSSVLHSTQDLFLPFFSNV

TWFHAIHVSGTNGTKRFDNPVLPFNDGVYFASTEKSNIIRGWIFGTTLDS

KTQSLLIVNNATNVVIKVCEFQFCNDPFLGVYYHKNNKSWMESEFRVYSS

ANNCTFEYVSQPFLMDLEGKQGNFKNLREFVFKNIDGYFKIYSKHTPINL

VRDLPQGFSALEPLVDLPIGINITRFQTLLALHRSYLTPGDSSSGWTAGA

AAYYVGYLQPRTFLLKYNENGTITDAVDCALDPLSETKCTLKSFTVEKGI

YQTSNFRVQPTESIVRFPNITNLCPFGEVFNATRFASVYAWNRKRISNCV

ADYSVLYNSASFSTFKCYGVSPTKLNDLCFTNVYADSFVIRGDEVRQIAP

GQTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVVV

LSFELLHAPATVCGPKKSTNLVKNKCVNFNFNGLTGTGVLTESNKKFLPF

QQFGRDIADTTDAVRDPQTLEILDITPCSFGGVSVITPGTNTSNQVAVLY

QDVNCTEVPVAIHADQLTPTWRVYSTGSNVFQTRAGCLIGAEHVNNSYEC

DIPIGAGICASYQTQTNSPRRARSVASQSIIAYTMSLGAENSVAYSNNSI

AIPTNFTISVTTEILPVSMTKTSVDCTMYICGDSTECSNLLLQYGSFCTQ

LNRALTGIAVEQDKNTQEVFAQVKQIYKTPPIKDFGGFNFSQILPDPSKP

SKRSFIEDLLFNKVTLADAGFIKQYGDCLGDIAARDLICAQKFNGLTVLP

PLLTDEMIAQYTSALLAGTITSGWTFGAGAALQIPFAMQMAYRFNGIGVT

QNVLYENQKLIANQFNSAIGKIQDSLSSTASALGKLQDVVNQNAQALNTL

VKQLSSNFGAISSVLNDILSRLDKVEAEVQIDRLITGRLQSLQTYVTQQL

IRAAEIRASANLAATKMSECVLGQSKRVDFCGKGYHLMSFPQSAPHGVVF

LHVTYVPAQEKNFTTAPAICHDGKAHFPREGVFVSNGTHWFVTQRNFYEP

QIITTDNTFVSGNCDVVIGIVNNTVYDPLQPELDSFKEELDKYFKNHTSP

DVDLGDISGINASVVNIQKEIDRLNEVAKNLNESLIDLQELGKYEQYIKW

PWYIWLGFIAGLIAIVMVTIMLCCMTSCCSCLKGCCSCGSCCKFDEDDSE

PVLKGVKLHYT

The present kits can further comprises a binder that binds to an antibody of a subject to an infectious organism. Any suitable binder can be used. For example, the binder can be a protein or polypeptide binder, e.g., an antibody, or a non-protein binder, e.g., a binder comprising a peptide or nucleic acid scaffold, such as an aptamer. In some embodiments, the binder can comprise a detectable label, e.g., a colorimetric, radioactive, enzymatic, luminescent or fluorescent label.

The present kits can further comprise a binder that binds to an antibody of a subject to an infectious organism, the binder comprising a first member of a binding pair. In some embodiments, the present kits can further comprise a second member of the binding pair. In some embodiments, the second member can comprises a detectable label, e.g., a colorimetric, radioactive, enzymatic, luminescent or fluorescent label. Any suitable binder pair can be used. For example, the binding pair can comprise an antigen-antibody binding pair, an avidin (streptavidin)/biotin binding pair, a peptide-binder pair, or a DNA-binder pair.

The present kits can comprise any suitable detectable label. For example, the present kits can comprise a colorimetric, radioactive, enzymatic, luminescent or fluorescent label. In some embodiments, the present kits comprises a fluorescent label.

The present kits can further comprise a particle, e.g., a bead. Any suitable particle(s) can be used. In some embodiments, the present kits can comprise a magnetic particle, a nanoparticle, or a polystyrene particle.

In some embodiments, the present kits can comprise a surface on which an antigen of an infectious organism, or a fragment or analog thereof, can be immobilized to allow binding between the antibody to the antigen of the infectious organism, and the antigen of the infectious organism, or a fragment or analog thereof, to form a complex between the antibody and the antigen, or a fragment or analog thereof, on the surface. Any suitable surface can be used. For example, the surface can be part of a solid surface, a planar surface or a porous surface, or a microtiter plate, e.g., a 96/384 well microtiter plate, a microtiter plate comprising microwells, a microfluidic device, or a microfluidic device comprising an array of femtoliter reaction wells. In some embodiments, the present kits can be configured for an ELISA format.

The present kits can comprise any suitable calibrator antibody. For example, the present kits can comprise a calibrator antibody that is a chimeric antibody, or a fragment thereof. In some embodiments, the calibrator antibody can comprise a constant region of a species of a subject and a variable region component of a different species.

The present kits can comprise a single calibrator antibody or a plurality of calibrator antibodies for generating a calibration data set. The present kits can comprise a calibrator antibody (or a plurality of calibrator antibodies) at any suitable multiple concentrations or levels for generating a calibration data set. In some embodiments, the present kits can comprise a calibrator antibody (or a plurality of calibrator antibodies) at concentrations or levels ranging from about 0.001 ng/mL to about 10,000 ng/mL, e.g., at about 0.001 ng/mL, 0.01 ng/mL, 0.1 ng/mL, 1 ng/mL, 10 ng/mL, 100 ng/mL, 1,000 ng/mL, 10,0000 ng/mL, or any subrange thereof.

The present kits can comprise any suitable calibrator antibody. For example, the calibrator antibody can comprise an intact antibody, e.g., an intact chimeric antibody. In another example, the antibody can be a recombinant, e.g., a recombinant chimeric antibody, or a fragment thereof.

In some embodiments, the present kits can be configured for quantitatively detecting a human antibody to an infectious organism, and the calibrator antibody, or a fragment thereof, can comprise a constant region of a human antibody. In some embodiments, the present kits can be configured for quantitatively detecting a human antibody to an infectious organism, and the calibrator antibody can comprise a fully human antibody, a humanized antibody, a humanized chimeric antibody, or a fragment thereof.

In some embodiments, the calibrator antibody, or a fragment thereof, can comprise a variable region component or a variable region of a human, mouse, rat, rabbit, goat, pig, chicken, alpaca, donkey, sheep, hamster, Armenian hamster, golden Syrian hamster, guinea pig, cow, horse, llama, dog, cat, monkey, turkey, duck, recombinant, or mixed species antibody. In some embodiments, the calibrator antibody can comprise a monoclonal antibody, or a fragment thereof.

The present kits can be configured for quantitatively detecting any suitable class of antibody to an infectious organism. For example, the present kits can be configured for quantitatively detecting a class of IgA, IgD, IgE, IgG, or IgM antibody to an infectious organism. In some embodiments, the present kits can be configured for quantitatively detecting a class of human IgA, IgD, IgE, IgG, or IgM antibody to an infectious organism. The present kits can be configured for quantitatively detecting a subclass (or isotype) of antibody to an infectious organism.

In some embodiments, the present kits can be configured for quantitatively detecting a class of IgA antibody to an infectious organism, and wherein the binder binds to the IgA antibody in the complex and the calibrator antibody is a chimeric IgA antibody. In some embodiments, the present kits can be configured for quantitatively detecting a class of IgD antibody to an infectious organism, and wherein the binder binds to the IgD antibody in the complex and the calibrator antibody is a chimeric IgD antibody. In some embodiments, the present kits can be configured for quantitatively detecting a class of IgE antibody to an infectious organism, and wherein the binder binds to the IgE antibody in the complex and the calibrator antibody is a chimeric IgE antibody. In some embodiments, the present kits can be configured for quantitatively detecting a class of IgG antibody to an infectious organism, and wherein the binder binds to the IgG antibody in the complex and the calibrator antibody is a chimeric antibody, e.g., a chimeric humanized mouse IgG antibody or a chimeric humanized mouse IgG specific for COVID-19 S1 spike protein. In some embodiments, the present kits can be configured for quantitatively detecting a class of IgM antibody to an infectious organism, and wherein the binder binds to the IgM antibody in the complex and the calibrator antibody is a chimeric IgM antibody.

The present kits can be configured for quantitatively detecting any suitable number of antibody or to antibodies an infectious organism. In some embodiments, the present kits can be configured for quantitatively detecting a single antibody to an infectious organism. In some embodiments, the present kits can be configured for quantitatively detecting multiple antibodies to an infectious organism. In some embodiments, the present kits can be configured for quantitatively detecting multiple antibodies to a single infectious organism. In some embodiments, the present kits can be configured for quantitatively detecting multiple antibodies to multiple infectious organisms. In some embodiments, the present kits can be configured for quantitatively detecting multiple antibodies in the same class or subclasses (or isotypes).

In some embodiments, the present kits can be configured for quantitatively detecting multiple antibodies in different subclasses (or isotypes). In some embodiments, the present kits can be configured for quantitatively detecting multiple antibodies in different classes. In some embodiments, the present kits can be configured for quantitatively detecting multiple antibodies in different subclasses (or isotypes).

In some embodiments, the present kits can be configured for quantitatively detecting an antibody to SARS-CoV-2 in a human. In some embodiments, the present kits can be configured for quantitatively detecting an IgG antibody to SARS-CoV-2 in a human.

In some embodiments, the present kits can be configured for quantitatively detecting an antibody, e.g., an IgG antibody, to SARS-CoV-2 protein mutant(s) or variant(s) in a subject or a human. The SARS-CoV-2 protein mutant(s) or variant(s) include mutant(s) with amino acid addition(s), deletion(s) and/or substitution(s). In the kits for quantitatively detecting an antibody, e.g., an IgG antibody, to SARS-CoV-2 protein mutant(s) or variant(s), the corresponding SARS-CoV-2 protein mutant(s) or variant(s) can be used as an antigen, or a fragment thereof, to contact with an antibody in a subject or a human.

In some embodiments, the present kits can be configured for quantitatively detecting an antibody to SARS-CoV-2 spike (S) protein in a subject or a human. In some embodiments, the present kits can be configured for quantitatively detecting an IgG antibody to spike (S) protein in a subject or a human. In some embodiments, the present kits can be configured for quantitatively detecting an antibody, e.g., an IgG antibody, to SARS-CoV-2 spike (S) protein mutant(s) or variant(s) in a subject or a human. The SARS-CoV-2 protein spike (S) mutant(s) or variant(s) include mutant(s) or variant(s) with amino acid addition(s), deletion(s) and/or substitution(s). Exemplary spike (S) protein mutant(s) or variant(s) include D614G, L5F, L8V, V367F, G476S, V483A, H49Y, Y145H/del, Q239K, A831V, D839Y/N/E, P1263L, and/or a combination thereof (See e.g., bioRxiv preprint doi: https://doi.org/10.1101/2020.04.29.069054; posted May 5, 2020). In the kits for quantitatively detecting an antibody, e.g., an IgG antibody, to SARS-CoV-2 spike (S) protein mutant(s) or variant(s), the corresponding SARS-CoV-2 spike (S) protein mutant(s) or variant(s) can be used as an antigen, or a fragment thereof, to contact with an antibody in a subject or a human.

The present kits can be configured to be conducted or performed with any suitable throughput. For example, the present kits can be configured to have a throughput ranging from about 10 tests/hour to about 100 tests/hour, e.g., about 10 tests/hour, 20 tests/hour, 30 tests/hour, 40 tests/hour, 50 tests/hour, 60 tests/hour, 70 tests/hour, 80 tests/hour, 90 tests/hour, 100 tests/hour, or any subrange thereof.

The present kits can be configured to be conducted or performed in any suitable time period. For example, the present kits can be configured to be conducted in a time period from about 20 minutes to about 300 minutes, e.g., about 20 minutes, 30 minutes, 40 minutes, 50 minutes, 60 minutes, 70 minutes, 80 minutes, 90 minutes, 100 minutes, 150 minutes, 200 minutes, 250 minutes, 300 minutes, or any subrange thereof, till first result or results of a set number of tests, e.g., about 250-300 samples, are obtained.

In some embodiments, the present kits can be configured for quantitatively detecting an antibody to COVID-19 S1 spike protein, e.g., a class of IgG antibody to COVID-19 S1 spike protein, and has a detection cut-off from about 2 ng/mL to about 5 ng/mL, e.g., about 2 ng/mL, 3 ng/mL, 4 ng/mL, 5 ng/mL, or any subrange thereof.

In some embodiments, the present kits can be configured for quantitatively detecting an antibody to COVID-19 S1 spike protein, e.g., a class of IgG antibody to COVID-19 S1 spike protein, and have a precision (or CV) ranging from about 3% to about 30%, e.g., about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or any subrange thereof. In some embodiments, the present kit can be configured to have a between-run precision CV ranging from 5% to about 20%, e.g., about 5%, 6%, 7%, 8%, 9%, 10%, 11%, 12%, 13%, 14%, 15%, 16%, 17%, 18%, 19%, 20%, or any subrange thereof. In some embodiments, the present kit can be configured to have a within-run precision CV ranging from 3% to 30%, e.g., about 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or any subrange thereof.

In some embodiments, the present kits can be configured for quantitatively detecting an antibody to COVID-19 S1 spike protein, e.g., a class of IgG antibody to COVID-19 S1 spike protein, and can have a sensitivity ranging from about 2 fg/mL to about 1 ng/mL, e.g., about 2 fg/mL, 10 fg/mL, 100 fg/mL, 1,000 fg/mL, 1,000 fg/mL, 0.01 ng/mL, 0.1 ng/mL, 1 ng/mL, or any subrange thereof.

In some embodiments, the present kits can be configured for quantitatively detecting an antibody to COVID-19 S1 spike protein, e.g., a class of IgG antibody to COVID-19 S1 spike protein, and can have a specificity, e.g., IgG specificity, ranging from about 70% to about 100%, e.g., about 70%, 75%, 80%, 85%, 90%, 95%, 96%, 97%, 98%, 99%, 100%, or any subrange thereof.

In some embodiments, the present kits can be configured for quantitatively detecting an antibody to COVID-19 S1 spike protein, e.g., a class of IgG antibody to COVID-19 S1 spike protein, and the quantitation results from comparable serum and plasma samples are within from about 0% to about 20% of each other, e.g., about 0%, 1%, 2%, 3%, 4%, 5%, 6%, 7%, 8%, 9%, 10%, 11%, 12%, 13%, 14%, 15%, 16%, 17%, 18%, 19%, 20%, or any subrange thereof.

The present kits can be configured for any suitable purposes or utilities. For example, the present kits can be configured to aid or facilitate diagnosis, prognosis, risk assessment, stratification and/or treatment monitoring of infection by an infectious organism in a subject, and/or for research and drug/vaccine discovery and/or development.

The present kits can be configured to assess an immune response to an infectious organism in a subject. For example, the present kits can be configured to assess an immune response to SARS-CoV-2 in a subject, e.g., a human subject or patient.

The present kits can be configured to assess past infection by an infectious organism in a subject. For example, the present kits can be configured to assess past infection by SARS-CoV-2 in a subject, e.g., a human subject or patient.

The present kits can be configured to assess IgG seroconversion to an infectious organism in a subject. For example, the present kits can be configured to assess IgG seroconversion to SARS-CoV-2 in a subject, e.g., a human subject or patient.

D. Description of Exemplary Device

D.1. Assay Biological Principles

The Simoa COVID-19 IgG Antibody Test is a 3-step paramagnetic microbead-based sandwich ELISA. In the first step, sample is drawn from a sample tube by the instrument pipettor and mixed with COVID-19 spike protein coated paramagnetic capture beads in a reaction cuvette. IgG antibodies in the sample that are specific to COVID-19 spike protein are bound by the capture beads. After an incubation, capture beads are collected with a magnet, and washed. Biotinylated anti-human IgG detector antibodies are then mixed with the capture beads, and the detector antibodies bind to the captured sample IgG. Following a second wash, a conjugate of streptavidin-β-galactosidase (SBG) is mixed with the capture beads. SBG binds to the biotinylated detector antibodies, resulting in enzyme labeling of captured sample IgG. After a third wash, the capture beads are resuspended in a resorufin β-D-galactopyranoside (RGP) substrate solution. Digital processing occurs when beads are transferred to the Simoa array disc which is composed of microarrays of femtoliter reaction wells. Individual capture beads are then sealed within microwells in the array through the addition of oil, which forms a liquid seal trapping the labeled immunocomplexes and RGP within the wells. If anti-spike IgG from the sample has been captured and labeled, the β-galactosidase hydrolyzes the RGP substrate into a fluorescent product that provides the signal for measurement. The concentration of IgG in unknown samples is interpolated from a calibration curve obtained by 4-parameter logistical regression fitting. Total time to first result is 80 minutes.

D.2. Reagents and Test Components

D.2.1. Simoa COVID-19 IgG Antibody Test Kit

The following Table 1 summarizes the reagent components of COVID-19 IgG antibody test kit:

| Bead Reagent | 1 bottle (4.5 mL) | COVID-19 spike protein (recombinant) coated capture beads in Tris buffer with a protein stabilizer (bovine) and a surfactant. Preservative: ProClin 300. |
| --- | --- | --- |
| Detector Reagent | 1 bottle (11.8 mL) | Biotinylated anti-human IgG antibody (mouse monoclonal) in phosphate buffer with a protein stabilizer (bovine) and a surfactant. Preservative: ProClin 300. |
| SBG Reagent | 1 bottle (11.8 mL) | Conjugate of streptavidin-β-galactosidase (SBG) in phosphate buffer with a protein stabilizer (bovine). Preservative: ProClin 300. |
| Sample Diluent | 2 bottles (13.1 mL) | Phosphate buffer with a protein stabilizer (bovine), a heterophilic blocker, and a surfactant. Preservative: Sodium azide. |
| RGP Reagent | 2 bottles (3.4 mL) | Resorufin β-D-galactopyranoside (RGP) in phosphate buffer with a surfactant. |

The 2-8C shelf life of kit reagents has not yet been established.

D.2.2. Simoa COVID-19 IgG Calibrators 8 vials (1 mL each) of Anti-COVID-19 IgG Calibrators. Calibrator A is phosphate buffer with a protein stabilizer (bovine), a surfactant, and sodium azide as a preservative. Calibrators B through H are chimeric humanized mouse IgG (specific for COVID-19 S1 spike protein) in Calibrator A buffer. The chimeric humanized mouse IgG is a monoclonal antibody combining the constant domains of the human IgG1 molecule with mouse variable regions. The variable region was obtained from a mouse immunized with purified, recombinant SARS-CoV S1 spike protein and produced using recombinant antibody technology. The calibrators (and controls) are value-assigned on a lot-by-lot basis comparing to frozen primary reference standards. Manufacturing tolerances for the value-assignment step ensure reproducibility across lots. Primary reference standards are chimeric humanized mouse IgG (specific for COVID-19 S1 spike protein) in human serum. No international reference material is available for anti-COVID-19 IgG, and the chimeric humanized anti-COVID-19 IgG Calibrators are stored frozen and thawed at the point of use. Concentrations of kit calibrator levels below are approximations based on typical values (see Table 2 below):

| Calibrator | IgG concentration (ng/mL)* |
| --- | --- |
| A | 0 |
| B | 0.02 |
| C | 0.1 |
| D | 0.4 |
| E | 2.0 |
| F | 10 |

| Calibrator | IgG concentration (ng/mL)* |
|---|---|
| G | 50 |
| H | 250 |

*Tentative target levels based on current data. Actual concentrations vary slightly from lot-to-lot. Sample results based on chimeric calibrators are proportional to antibody titer, but they may not reflect absolute concentrations of native anti-COVID IgG.

The frozen shelf life of kit calibrators has not yet been established.

D.2.3. Simoa COVID-19 IgG Controls 2 bottles (1.0 mL each) of Anti-COVID-19 IgG Controls in phosphate buffer with a protein stabilizer (bovine), a surfactant, and sodium azide as a preservative. Controls provide a check on calibration curve validity and are prepared as per Anti-COVID-19 IgG Calibrators, with value-assignments made on a lot-by-lot basis through calibration to primary reference calibrators. Controls are prepared at the following approximate concentrations (see Table 3 below):

| Control | IgG concentration (g/mL)* |
|---|---|
| 1 (negative) | 0.5 |
| 2 (positive) | 20 |

*Tentative target levels based on current data. Actual concentrations vary slightly from lot-to-lot. Sample results based on chimeric calibrators are proportional to antibody titer, but they may not reflect absolute concentrations of native anti-COVID IgG.

The negative control level was chosen to be below the preliminary cut-off (0.02 ng/mL) and to be representative of non-specific binding of IgG in individuals uninfected by COVID-19. The positive control was chosen to be in the lower range of reactivity (lower 0.2% of the dynamic range). As with the calibrators, controls are stored frozen and thawed at the point of use. The frozen shelf life of kit controls has not yet been established.

D.2.4. Other Test Components

Non-specific reagent components are required for the HD-X system to run the Simoa COVID-19 IgG assay. These are listed in Table 4 below:

| | |
|---|---|
| System Wash Buffer 1 | Phosphate buffer with surfactant. Preservative: ProClin 300. |
| System Wash Buffer 2 | Phosphate buffer. Preservative: ProClin 300. |
| Sealing Oil | Synthetic fluorinated polymer |

These components are obtained directly from Quanterix.

D.3. HD-X Analyzer

D.3.1. Instrument and Operation

Figure 1:
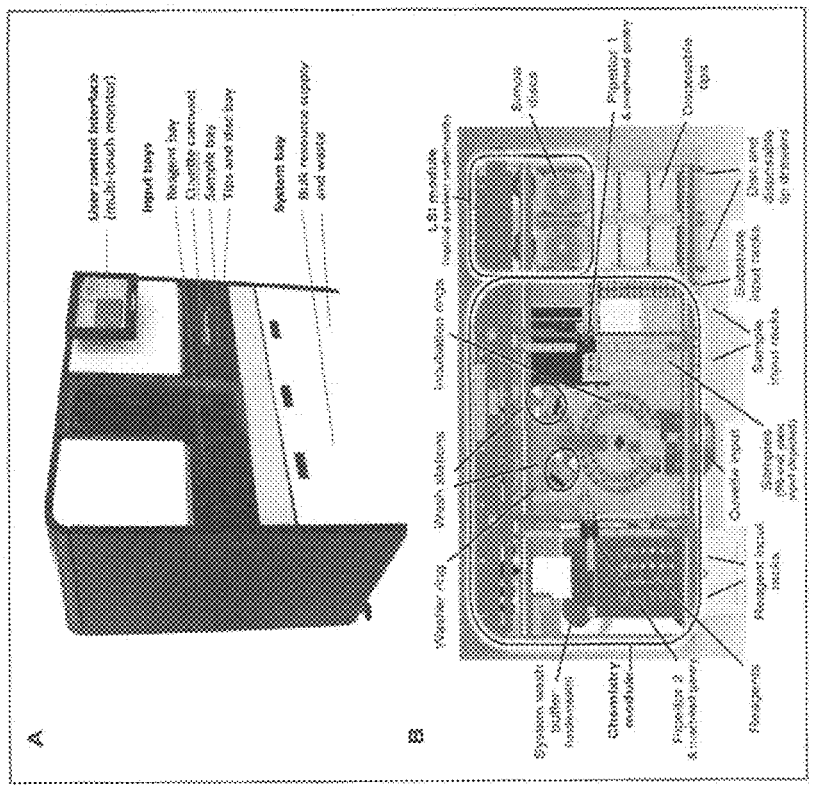
FIG. 1 illustrates an exemplary Simoa HD-X system or analyzer.

The HD-X system is manufactured by Stratec Biomedical Systems (Birkenfeld, Germany) under ISO 13485. The instrument is a floor-standing fully automated immunoassay analyzer consisting of five main functional areas (FIG. 1): (1) input bays for addition of disposables (tips, cuvettes, array discs), reagent kits, and samples; (2) a system bay for bulk resources and waste; (3) the user control interface (integrated flat-screen monitor and computer); (4) a chemistry module that contains rotating incubation and wash rings; and (5) the Simoa load-seal-image (LSI) module. General pipetting operations are provided by an overhead gantry with two x-y-z pipettors (FIG. 1B): a disposable-tip pipetter (pipettor 1, sample and reaction mixture handling) and a fixed-tip pipettor (pipettor 2, reagent pipetting). The input bays are accessed from the front of the instrument, while the reagent bay contains four lanes for insertion of reagent kits via four independent reagent racks. The LSI module is the subsystem that performs proprietary operations that enable single-molecule counting and ultra-high sensitivity.

The HD-X system was designed to minimize operator intervention. To operate the system, the user interfaces routinely with the input and system bays and the flat-screen monitor. Test orders and run load lists are entered through the touchscreen monitor. Samples, assay reagents, and disposables are loaded into their respective bays. The input bays are accessed from the front of the instrument. Samples can be loaded either as tubes (up to 96) or in microtiter plates (up to four 96-well plates). When sample tubes are added to a sample rack and inserted into a lane in the sample bay, an integrated barcode reader reads sample ID barcodes as the rack is inserted.

During an assay run, the instrument utilizes three dedicated disposables for each sample (two disposable tips, one reaction cuvette) and one array on the 24-array disposable Simoa disc. Pipette tips are acquired and disposed of by the sample pipettor, and reaction cuvettes are retrieved for each sample from the cuvette stacks in the cuvette bay. When tests are completed, reaction cuvettes are automatically removed to the solid-waste container in the system bay. When processing is complete for each sample, results are calculated from image files by software algorithms that include quality control (QC) checks for data quality. Values are flagged if they are not within certain preset parameters (e.g., out of calibration range). The assay sequence is aborted if certain control variables are out of range. Immunoassays and data reduction are performed by the system with a steady state throughput of 66 tests/h. Maximum walkaway time is 4.5 hours before resources need to be replenished or liquid waste needs to be emptied.

To run the Simoa COVID-19 IgG Antibody assay, users transfer thawed, ready-to-use calibrators and samples to the system by either an ELISA plate or by adding sample tubes to a tube rack. Before a run can be initiated, users must also load required assay reagents, system buffers/consumables and set up the run load list in the instrument software. Upon starting the run, the user can walk away until the assay results are ready in about 90 minutes.

D.3.2. Instrument Consumables

The three plastic consumables used by the HD-X system are (see Table 5 below):

| Consumable | Description | Manufacturer |
|---|---|---|
| Simoa Disc | Single molecule array disc enabling single molecule counting (proprietary technology) | Stratec Biomedical/ Sony DADC |
| Reaction vessels | Cuvettes in which immunoassay chemistry steps are performed | Stratec Biomedical |
| Pipette tips | Low-retention pipettor tips to eliminate cross-contamination between samples during processing. | Axygen, Corning Life Sciences |

Simoa Disc.

The Simoa disc has been described in detail elsewhere (3). In brief, it is a DVD-sized disc composed of 24 arrays of femtoliter-sized microwells, arranged radially to enable fabrication using Blu-ray manufacturing processes. Singulation of microbeads is a critical requirement of Simoa technology, and the geometry of the microwells is sufficient to accommodate only single microbeads.

Cuvettes.

The system uses a V-shaped, four-sided plastic reaction cuvette for assay processing steps from initial analyte capture to final concentration of microbeads for transfer to the Simoa disc. The V shape facilitates maximum precision of low-volume fluid handling and pellet resuspension by the system pipettor by minimizing cuvette dead volume.

Pipettor Tips.

Manufactured using a polished mold to minimize liquid retention in the tip and ensure accurate sample volumes. During sample processing, one tip is used for sample transfer, and a second tip is used for bead resuspension and transfer from the cuvette to the Simoa disc. The manufacturers of these instrument consumables are ISO 13485 certified. These consumables are obtained directly from Quanterix.

D.3.3. Instrument Software

The common and technology-specific subsystems of the instrument are controlled by a real-time software scheduling processor. The software controlling the system includes inventory tracking of system consumables, user-editable assay parameters and dilutions, automatic data reduction, customizable report formats, and network connectivity. Data reduction capabilities include calibration curve fitting with level-by-level weighting, calibration curve refitting, curve fitting residuals for feedback on fitting accuracy, and conversion of raw signal to concentrations. While the instrument is currently for RUO, it was designed to be easily convertible to a more controlled IVD instrument.

The level of safety concern for the Simoa COVID-19 IgG antibody test and the HD-X system is Moderate. The assay results will be provided to healthcare professionals to use in conjunction with other established laboratory results and clinical information. A falsely elevated or depressed Simoa COVID-19 IgG antibody result has a low potential to influence interpretation of immune status and back-to-work dispositioning regarding infection risk. (Note: Labeling will caution against the use of a single Simoa COVID-19 IgG antibody result for infection diagnosis or risk dispositioning independent of other laboratory/clinical disease activity monitoring modalities.)

D.4. Assay Performance Studies

D.4.1. Performance Data

Figure 2:
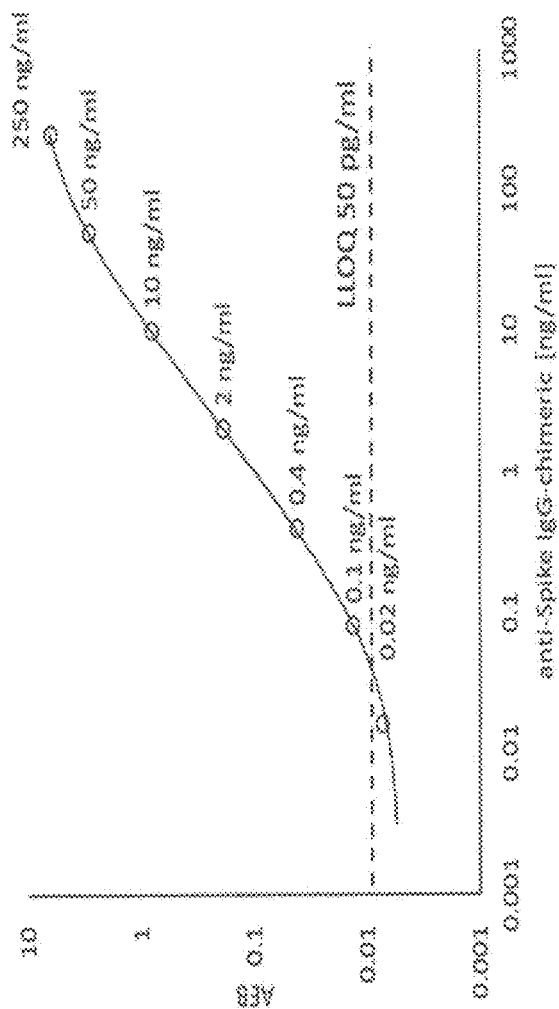
FIG. 2 illustrates an exemplary representative calibration curve of Quanterix SARS-CoV-2 IgG Antibody Test using humanized chimeric anti-SARS-CoV-2 IgG calibrators. Chimeric IgG calibration serves as a surrogate in the absence of consensus IgG standards.

A representative calibration curve for IgG quantification is depicted in FIG. 2. Representative calibration curve of Quanterix SARS-CoV-2 IgG Antibody Test using humanized chimeric anti-SARS-CoV-2 IgG calibrators. Chimeric IgG calibration serves as a surrogate in the absence of consensus IgG standards.

During the initial phase of assay development, 10 serum samples collected pre-pandemic (presumed to have no antibodies against SARS-CoV-2) and 25 serum samples from people with COVID-19 infection as confirmed by RNA RT-PCR were tested in the quantitative SARS-CoV-2 IgG antibody assay (FIG. 3). With a preliminary cut-off value of 2 ng/mL, the test exhibits 100% specificity and 90% sensitivity. SARS-CoV-2 IgG antibody concentrations for 25 pre-pandemic and 10 SARS-CoV-2 positive (based on RNA RT-PCR) serum samples are shown in FIG. 3. Specificity was 100%.

D.4.2. Studies Planned or in Progress

Studies planned or in progress include (see Table 6 below):

| Parameter | Validation Plan |
| --- | --- |
| Precision | Inter- and intra-assay precision for the positive control (PC) and the negative control (NC) samples will be calculated as the coefficient of variation (CV) for the back-calculated from the calibration curve concentration values. |
| Cross-reactivity/ analytical specificity | Serum samples from >100 people collected before pandemic (before December 2019) that are expected to be seronegative for SARS-CoV-2 and to have exposure to other coronaviruses and a high prevalence of vaccination against influenza, HBV, and other diseases) or viral exposure will be tested in the assay. If less than 98% specificity is observed, samples from people with known exposure to coronaviruses, influenza and other infectious agents listed below will be tested. Anti-alpha coronavirus (229E, NL63), anti-beta coronaviruses (OC43, HKU1), anti-influenzae, anti-HCV, anti-HBV, ANA, annti-respiratory syncytial virus, anti-rhinovirus (IgG and IgM). |
| IgG class Specificity | To demonstrate the IgG class specificity of the test, unlabeled anti-human IgG will be used to demonstrate competition with the labeled anti-human-IgG and subsequent decrease in the IgG signal. |
| Matrix equivalency | To evaluate the equivalence for serum and plasma samples, 5 sets of matched serum and plasma samples negative for SARS-CoV-2 IgG will be spiked with the same amount of samples known to have high concentration of SARS-CoV-2 IgG. Samples will be spiked at three levels: below clinical threshold, at low IgG levels (low positive) and high IgG levels (high positive) and evaluated in the assay. Matrices will be deemed comparable if the concentration results will be within 25% of each other |
| Clinical Validity | >100 serum and plasma samples collected before SARS-CoV-2 pandemic (before December 2019) that are expected to be seronegative for SARS-CoV-2 will be used as negative controls. >60 serum and plasma samples from people confirmed to be infected by SARS-CoV-2 using RT-PCR will be used as positive controls. Positive and negative percent agreement between the SARS-CoV-2 IgG serology test result and comparator RT-PCR method will be calculated. |

REFERENCES CITED

1. Rissin D M, Kan C W, Campbell T G, Howes S C, Fournier, D R, Song L, et al. D. C. Single-molecule enzyme-linked immunosorbent assay detects serum proteins at subfemtomolar concentrations. Nature Biotechnol 2010; 28:595-9.
2. Wilson D H, Rissin D M, Kan C W, Fournier D R, Piech T, Campbell T G, et al. The Simoa HD-1 Analyzer: a novel fully automated digital immunoassay analyzer with single molecule sensitivity and multiplexing. J Lab Autom. 2016 August; 21(4):533-47.

3. Kan C W, Rivnak A J, Campbell T G, Piech T, Rissin D M, Mosl M, et al. Isolation and detection of single molecules on paramagnetic beads using sequential fluid flows in microfabricated polymer array assemblies. Lab Chip 2012; 12:977-85.

E. Exemplary Embodiment

Simoa Quantitative SAR-CoV-2 IgG Antibody Test
Intended Use
The Simoa Quantitative SARS-CoV-2 IgG Antibody Test is an automated paramagnetic microbead-based immunoassay intended for the quantitative detection of human IgG antibodies to SARS-CoV-2 in serum or EDTA plasma using the HD-X immunoassay system. The test detects and quantitates IgG antibodies as indicative of an immune response to SARS-CoV-2 in patients suspected of previous SARS-CoV-2 infection, or for the detection of IgG seroconversion in patients following known recent SARS-CoV-2 exposure. The test is an aid in the diagnosis of patients suspected of prior SARS-CoV-2 in conjunction with clinical presentation and the results of other laboratory tests. Results from Simoa Quantitative SARS-CoV-2 IgG Antibody Test should not be used as the sole basis for diagnosis and should not be used for the diagnosis of patients with acute SARS-CoV-2 infection.

Testing is limited to laboratories certified under the Clinical Laboratory Improvement Amendments of 1988 (CLIA), 42 U.S.C. § 263a, to perform moderate and high complexity tests.

Results are for the detection and quantitation of IgG antibodies against SARS-CoV-2. Reactive results could occur after infection and can be indicative of acute, or recent or past infection. Laboratories within the United States and its territories are required to report all reactive results to the appropriate public health authorities.

Non-reactive results do not preclude SARS-CoV-2 infection and should not be used as the sole basis for patient management decisions. Results must be combined with clinical observations, patient history, and epidemiological information. The sensitivity of the Simoa Quantitative SARS-CoV-2 IgG Antibody Test early after infection is unknown. False reactive results may occur due to cross-reactivity from pre-existing antibodies or other possible causes. At this time, it is unknown for how long antibodies to SARS-CoV-2 virus may persist following infection.

The Simoa Quantitative SARS-CoV-2 IgG Antibody Test is only for use under the Food and Drug Administration's Emergency Use Authorization.

Summary and Explanation of Test
Severe Acute Respiratory Syndrome Coronavirus 2 (SARS-CoV-2) is a recently identified coronavirus strain responsible for the Coronavirus Disease 2019 (COVID-19) and pandemic. SARS-CoV-2 emerged in China in December 2019 and is transmitted mainly through droplets and surface contact routes. The virus infects human cells through interaction between angiotensin converting enzyme 2 (ACE2) on respiratory cells and spike or S-protein on the outer envelope of the virion particle. COVID-19 affects people in different ways. Symptoms can include signs and symptoms of acute respiratory illness, such as fever, cough, shortness of breath, but the infection can also be asymptomatic. Symptomatic, pre-symptomatic and asymptomatic infected individuals all can be sources for viral transmission. The current gold standard for diagnosis of SARS-CoV-2 infection is real-time reverse transcription polymerase chain reaction (rRT-PCR), which detects the presence of SARS-CoV-2 nucleic acid material in upper respiratory specimens, such as nasopharyngeal swab and oropharyngeal swab. In contrast, anti-SARS-CoV-2 antibody detection detects exposure to the virus after the host immune response and seroconversion. Classes of antibodies detected by antibody tests are generally IgM and IgG. SARS-CoV-2 immunity status assessment is expected to play an important role in understanding the pandemic and potential infection risk at an individual and population level. Immunity passports" in the context of COVID-19 (www.who.int/news-room/commentaries/detail/immunity-passports-in-the-context-of-covid-19).

Principles of the Procedure
The Simoa Quantitative SARS-CoV-2 IgG Antibody Test is a 3-step paramagnetic microbead-based sandwich ELISA that uses single molecule array (Simoa) technology. Rissin D M, Kan C W, Campbell T G, et al. Single-molecule enzyme-linked immunosorbent assay detects serum proteins at subfemtomolar concentrations. Nat Biotech 2010; 28:595-99. In the first step, sample is drawn from a sample tube by the instrument pipettor and mixed with COVID-19 spike protein coated paramagnetic capture beads in a reaction cuvette. IgG antibodies in the sample that are specific to COVID-19 spike protein are bound by the capture beads. After an incubation, capture beads are collected with a magnet, and washed. Biotinylated anti-human IgG detector antibodies are then mixed with the capture beads, and the detector antibodies bind to the captured sample IgG. Following a second wash, a conjugate of streptavidin-β-galactosidase (SBG) is mixed with the capture beads. SBG binds to the biotinylated detector antibodies, resulting in enzyme labeling of captured sample IgG. After a third wash, the capture beads are resuspended in a resorufin β-D-galactopyranoside (RGP) substrate solution. Digital processing occurs when beads are transferred to the Simoa array disc which is composed of microarrays of femtoliter reaction wells. Individual capture beads are then sealed within microwells in the array through the addition of oil, which forms a liquid seal trapping the labeled immunocomplexes and RGP within the wells. If anti-spike IgG from the sample has been captured and labeled, the β-galactosidase hydrolyzes the RGP substrate into a fluorescent product that provides the signal for measurement. The concentration of IgG in unknown samples is interpolated from a calibration curve obtained by 4-parameter logistical regression fitting. Total time to first result is 80 minutes.

For additional information on system and assay technology, refer to the Simoa HD-X Analyzer User Guide.

Reagents
Reagent Kit
Simoa Quantitative SARS-CoV-2 IgG Antibody Test kit (see Table 7 below):
Simoa Quantitative SARS-CoV-2 IgG Antibody Test kit

| | | |
|---|---|---|
| Bead Reagent | 1 bottle (4.4 mL) | SARS-CoV-2 spike protein (recombinant) coated capture beads in Tris buffer with a protein stabilizer (bovine) and a surfactant. Preservative: ProClin 300. |
| Detector Reagent | 1 bottle (12.3 mL) | Biotinylated anti-human IgG antibody (goat polyclonal) in phosphate buffer with a protein stabilizer (bovine) and a surfactant. Preservative: ProClin 300. |
| SBG Reagent | 1 bottle (12.3 mL) | Conjugate of streptavidin-β-galactosidase (SBG) in phosphate buffer with a protein stabilizer (bovine). Preservative: ProClin 300. |
| Sample Diluent | 4 bottles (30 mL ea) | Phosphate buffer with a protein stabilizer (bovine), a heterophilic blocker, and a surfactant. Preservative: Sodium azide. |

-continued

| | | |
|---|---|---|
| RGP Reagent | 2 bottles (3.4 mL) | Resorufin β-D-galactopyranoside (RGP) in phosphate buffer with a surfactant. |
| Calibrators A-H (0 plus 7 levels) | 8 vials (1 mL each) | Anti-SARS-CoV/CoV-2 IgG in phosphate buffer with a protein stabilizer (bovine), a surfactant, and sodium azide as a preservative. |
| Negative control | 1 vial (0.125 mL each) | Pooled normal human serum with ProClin 300 as a preservative. |
| Positive control | 1 vial (0125 mL each) | IgG antigen in pooled normal human serum with ProClin 300 as a preservative. |

Materials Required but not Provided

Materials Required but Not Provided include:

Simoa HD-X Analyzer

Simoa HD-X System Wash Buffer 1

Simoa HD-X System Wash Buffer 2

Simoa HD-X Sealing Oil

Simoa cuvettes

Simoa disposable pipettor tips; and

Simoa Discs.

Warnings and Precautions

For in vitro diagnostic and laboratory professional use. For emergency authorization use only Safety Precautions CAUTION: This product requires the handling of human specimens. It is recommended that all human-sourced materials be considered potentially infectious and be handled in accordance with the OSHA Standard on Bloodborne Pathogens. World Health Organization. Laboratory biosafety manual. Geneva: World Health Organization, 2004. Biosafety Level 2 or other appropriate biosafety practices should be used for materials that contain or are suspected of containing infectious agents. Clinical and Laboratory Standards Institute. Protection of laboratory workers from occupationally acquired infections: Approved guideline, 3rd ed. CLSI Document M29-A3. Wayne, Pa.: Clinical and Laboratory Standards Institute, 2005.

Simoa reagents contain methylisothiazolones, which are components of ProClin and are classified per applicable European Community (EC) Directives as: Irritant (Xi). The following are the appropriate Risk (R) and Safety (S) phrases.

Simoa reagents contain methylisothiazolones, which are components of ProClin and are classified per applicable European Community (EC) Directives as: Irritant (Xi). The following are the appropriate Risk (R) and Safety (S) phrases.

R43 May cause sensitization by skin contact.

S24 Avoid contact with skin.

S35 This material and its container must be disposed of in a safe way.

S37 Wear suitable gloves.

S46 If swallowed, seek medical advice immediately and show this container or label.

For a detailed discussion of safety precautions during instrument operation, refer to the Simoa HD-X Analyzer User Guide.

Package insert instructions must be carefully followed. Reliability of assay results cannot be assured if there are deviations from the instructions in this package insert.

Handling Precautions

Handling Precautions:

Do not use reagent kits beyond the expiration date. When stored and handled as directed, reagents and calibrator are stable until the expiration date Do not pool reagents within a kit or between reagent kits.

Remaining Simoa reagents should be removed from the instrument upon completion of the assay run and stored at 2-8° C. upright with caps on.

Calibrators and controls are 1-time use; any remaining material should be discarded appropriately.

Do not attempt to reuse tips, cuvettes, or Simoa Discs, as this will cause significant data quality deterioration.

Storage Instructions

Storage Instructions:

Simoa Quantitative SARS-CoV-2 IgG Antibody Test reagents must be stored at 2-8° C. in an upright position; see, FIG. 15A.

Simoa Quantitative SARS-CoV-2 IgG Antibody Test calibrators and controls must be stored at −80° C. and should be kept upright, see, FIG. 15B.

When stored and handled as directed, reagents and calibrators are stable until the expiration date.

The Simoa Quantitative SARS-CoV-2 IgG Antibody Test reagents should be removed from the instrument upon completion of the assay run and stored at 2-8° C. upright with caps on.

Indications of Reagent Deterioration

If a control sample returns a concentration value out of the expected range, this may indicate deterioration of reagents or errors in technique. Associated test results may be invalid and may require retesting. Assay recalibration may be necessary. Refer to the calibrators and controls section of this document.

Specimen Collection and Preparation for Analysis

Specimen Collection and Preparation for Analysis:

Insufficient sample processing may cause inaccurate results.

For optimal results, specimens should be free of fibrin, red blood cells, or other particulate matter. Do not use grossly hemolyzed specimens.

Specimens thawed after frozen storage must always be mixed THOROUGHLY by low-speed vortexing or inverting 10 times. Visually inspect the specimens. If layering or stratification is observed, continue mixing until specimens are visibly homogeneous.

Specimens may be stored for up to 24 hours at 2-8° C. prior to being tested. If testing will be delayed for more than 24 hours, specimens should be frozen at −20° C. or colder.

The Simoa HD-X Analyzer does not provide the capability to verify specimen type. It is the responsibility of the operator to verify that the correct specimen type is used in the Simoa Quantitative SARS CoV-2 IgG Antibody test.

For freshly drawn serum specimens, ensure that complete clot formation has taken place prior to centrifugation. If specimens are centrifuged before a complete clot forms, the presence of fibrin or particulate matter may cause erroneous results.

Centrifuge all specimens prior to assay. Centrifugation conditions should be sufficient to efficiently remove particulate matter and to clarify the sample, for example 5 minutes at 10,000 g for serum or plasma. Note that interfering levels of fibrin may be present in samples that do not have obvious or visible particulate matter.

Centrifuged specimens with a lipid layer on the top should be transferred to a secondary tube. Care must be taken to transfer only the clarified specimen without the lipemic material.

Serum and plasma should be immediately removed from the red cells (after centrifugation) and put in a separate tube that can then be aliquoted and frozen for future use. For freshly drawn serum specimens, ensure that complete clot formation has taken place prior to centrifugation.

For optimal results, inspect all samples for bubbles. Remove bubbles with an applicator stick prior to analysis. Use a new applicator stick for each sample to prevent cross-contamination.

Use caution when handling patient specimens to prevent cross-contamination. Use of disposable pipettes or pipette tips is recommended.

Multiple freeze-thaw cycles of specimens should be avoided.

Specimens with obvious microbial contamination should not be used.

Specimen stability in different storage conditions has not been validated for this assay.

Procedure

Assay Procedure

The Simoa Quantitative SARS-CoV-2 IgG Antibody Test assay definition must be downloaded from the customer portal and installed on the Simoa HD-X Analyzer prior to performing the assay. Note: Assay definitions for the Simoa HD-1 and HD-X are different and not interchangeable.

Calibrators, controls, and samples must be allowed to come to room temperature and mixed thoroughly before loading onto the Simoa HD-X Analyzer.

Simoa reagents must be allowed to come to room temperature before loading onto the Simoa HD-X Analyzer. This is not necessary if using the HD-X DX model, which is equipped with a cooling reagent bay.

To improve run-to-run reproducibility, solubilize RGP fully by heating at 30-37° C. with constant vigorous shaking for a minimum of 30 minutes. Refer to *TECH-0051: RGP Substrate Preparation for Simoa Assays* for more details.

Before loading on the Simoa HD-X Analyzer, the Bead Reagent bottle must be mixed to resuspend the capture beads that may have settled. To resuspend the beads, vortex for a minimum of 30 seconds.

Note: The bead diluent is formulated with an antifoam agent, but vortexing can still create foaming. If the foam does not dissipate within a few minutes, remove excess foam with a pipette prior to loading bead reagent onto the Simoa HD-X Analyzer.

Set up the assay run on the instrument (see the Simoa HD-X Analyzer User Guide). Load the Simoa Quantitative SARS-CoV-2 IgG Antibody Test reagents (Bead Reagent, Detector Reagent, SBG Reagent, Sample Diluent) into the reagent bay.

Load samples, calibrators, controls, and RGP into the sample bay. (Note: Only one bottle of RGP is needed per 96-sample run. One bottle of RGP may be used for multiple smaller runs, but total time on board the instrument should be limited to no more than 8 hours and one work shift.)

In the run set up screen, specify 'neat' protocol. The samples will be diluted off-line prior to running the assay, and the instrument will not perform additional pre-dilutions. Follow the guidelines in the Specimen Dilution Procedure section of this package insert to set up sample dilutions.

Replenish consumables and system resources as needed prior to initiating the run, as described in the Simoa HD-X Analyzer User Guide.

Initiate the run.

Specimen Dilution Procedure

The minimum sample volume needed depends on the number of replicates desired, and whether samples will be introduced to the instrument in tubes or Quanterix-supplied 96-well plates. If a sample tube is used, the type and volume of the tube may determine the dead volume. Samples introduced in 5-mL Nalgene Cryogenic sample tubes have a dead volume of 50 µL. Samples introduced in a Quanterix-supplied 96-well plate have a dead volume of 30 µL. Note: The maximum recommended sample volume for the Quanterix-supplied 96-well plates is 400 µL.

Treat specimens and assay Controls the same way.

Perform a 1:1000 pre-dilution of specimens and controls with Sample Diluent. Given the large dilution, it is recommended to perform the dilution in two steps to maximize pipetting accuracy. FIG. 16 illustrates an example of a 2-step dilution, 10 µL of sample can be diluted to 100 µL, followed by a subsequent dilution of a 10 µL aliquot of diluted sample to 1000 µL.

Note: If an alternative procedure is followed, volume transfers should be no less than 10 µL to achieve the best accuracy.

Note: If samples are left on board the instrument or pipetted samples are left on a lab bench for more than an hour, evaporation effects may influence the results depending on the volume of sample. As a general guideline, at room temperature and normal humidity, a 60 µL sample will lose approximately 5% of its weight per hour. A 120 µL sample may lose 5% of its weight in approximately 3 hours.

To minimize evaporation when using microtiter plates for sample input, Quanterix recommends use of X-Pierce Sealing Films (cat #XP-100). No other plate seal is compatible with the Simoa HD-1/HD-X Analyzer.

Calibration

To perform a Quantitative SARS-CoV-2 IgG Antibody Test calibration, test Calibrators A through H in duplicate or triplicate. A single sample of all levels of Quantitative SARS-CoV-2 IgG Controls must be tested to evaluate the assay calibration. Ensure that all that assay control values are within expected concentration ranges.

Once a Quantitative SARS-CoV-2 IgG Antibody Test calibration is accepted and stored, all subsequent samples may be tested without further calibration unless Controls are out of range or a reagent kit with a new lot number is used.

Preparing Calibrators

Calibrators should be brought to room temperature prior to pipetting. Do not heat the vial to accelerate thawing.

When the solution is fully thawed, THOROUGHLY mix by multiple gentle inversions or vortexing. Frozen protein solutions can partition during freezing, so complete mixing of thawed material is critical for accurate calibrators.

Preparing Controls

Controls should be brought to room temperature prior to pipetting. Do not heat the vial to accelerate thawing.

When the solution is fully thawed, THOROUGHLY mix by multiple gentle inversions or vortexing. Frozen protein solutions can partition during freezing, so complete mixing of thawed material is critical for accurate controls.

Controls should be included in each run and should follow the same dilution scheme selected for samples.

Quality Control Procedures

It is recommended that the Quantitative SARS-CoV-2 IgG Antibody Test Negative Control and Positive Control be included in every batch run to assess calibration curve storage integrity and run validity. If the results from one or more of the controls are outside an expected range, the stored calibration curve may no longer be valid, and the assay may need to be re-calibrated. The length of time calibration curves may be stored must be validated for each laboratory. Alternatively, calibration can be performed with every batch run. It is recommended that Controls be run with every calibration to assess calibration accuracy and run validity. Follow the specific quality control procedures in your laboratory.

Results

The Quantitative SARS-CoV-2 IgG Antibody Test utilizes a 4 Parameter Logistic Curve fit data reduction method to generate a calibration curve. Specimen results are interpolated from the calibration curve.

Interpretation of Results

Specimens with concentration values <0.77 µg/mL are considered nonreactive for IgG by the criteria of Quantitative SARS-CoV-2 IgG Antibody Test.

Specimens with concentration values ≥0.77 µg/mL are considered reactive for IgG by the criteria of Quantitative SARS-CoV-2 IgG Antibody Test.

A negative result may indicate that IgG antibodies are present in concentrations below the detection limit of the assay. This can occur during acute infection prior to seroconversion. A positive result indicates the presence of IgG antibodies to SARS-CoV-2 due to exposure to SARS-CoV-2.

Note: Some results may contain information in the Flags field. For a description of the flags that may appear in this field, refer to the Simoa HD-X Analyzer User Guide.

Limitations of the Procedure

For in vitro diagnostic use under Emergency Use Authorization Only.

Bacterial contamination of specimens may affect the test results.

Therapeutic doses of biotin can interfere with assays that utilize biotinylated reagents.

Heterophilic antibodies in human serum can react with reagent immunoglobulins, interfering with immunoassays. People routinely exposed to animals or animal serum products can be prone to this interference, and anomalous values may be observed.

Specimens may contain human anti-mouse antibodies (HAMA). Such specimens may show either falsely elevated or falsely depressed values when tested with assay kits that employ mouse monoclonal antibodies. Simoa reagents contain a component that reduces the effect of HAMA-reactive specimens.

Conditions of Authorization for the Laboratory

The Simoa Quantitative SARS-CoV-2 IgG Antibody Test Letter of Authorization, along with the authorized Fact Sheet for Healthcare Providers, the authorized Fact Sheet for Patients, and authorized labeling are available on the FDA website.

Specimens with concentration Authorized laboratories using the Simoa Quantitative SARS-CoV-2 IgG Antibody Test ("your product" in the conditions below), must adhere to the Conditions of Authorization indicated in the Letter of Authorization as listed below:

Authorized laboratories using your product will include with result reports of your product, all authorized Fact Sheets. Under exigent circumstances, other appropriate methods for disseminating these Fact Sheets may be used, which may include mass media.

Authorized laboratories using your product will use your product as outlined in the Instructions for Use. Deviations from the authorized procedures, including the authorized instruments, authorized clinical specimen types, authorized control materials, authorized other ancillary reagents and authorized materials required to use your product are not permitted.

Authorized laboratories that receive your product will notify the relevant public health authorities of their intent to run your product prior to initiating testing.

Authorized laboratories using your product will have a process in place for reporting test results to healthcare providers and relevant public health authorities, as appropriate.

Authorized laboratories will collect information on the performance of your product and report to DMD/OHT7-OIR/OPEQ/CDRH (via email: CDRH-EUA-Reporting@fda.hhs.gov) and Quanterix Corporation at www.Quanterix.com any suspected occurrence of false reactive or false non-reactive results and significant deviations from the established performance characteristics of your product of which they become aware.

All laboratory personnel using your product must be appropriately trained in automated immunoassay techniques and use appropriate laboratory and personal protective equipment when handling this kit and use your product in accordance with the authorized labeling. All laboratory personnel using the assay must also be trained in and be familiar with the interpretation of results of the product.

Quanterix Corporation, authorized distributors, and authorized laboratories using your product will ensure that any records associated with this EUA are maintained until otherwise notified by FDA. Such records will be made available to FDA for inspection upon request.

The letter of authorization refers to, "Laboratories certified under the Clinical Laboratory Improvement Amendments of 1988 (CLIA), 42 U.S.C. § 263a, to perform moderate and high complexity tests" as "authorized laboratories."

Performance Characteristics

Precision

Five precision panel members were prepared by serial dilution of 10 pooled SARS-CoV-2 positive (PCR+) patient sera. Controls were diluted in Sample Diluent, and 6 runs performed in triplicate across 4 HD-X instruments. Inter and intra-run precision is depicted in Tables 8 and 9 respectively:

TABLE 8

| Positive Pool Dilution | Run 1 (µg/mL) | Run 2 (µg/mL) | Run 3 (µg/mL) | Run 4 (µg/mL) | Run 5 (µg/mL) | Run 6 (µg/mL) | Avg (µg/mL) | Inter-run CV |
|---|---|---|---|---|---|---|---|---|
| 1 | 5.52 | 5.81 | 5.89 | 4.99 | 5.38 | 5.42 | 5.50 | 5.9% |
| 2 | 2.27 | 2.77 | 2.77 | 2.48 | 2.67 | 2.78 | 2.62 | 8.0% |
| 3 | 1.12 | 1.23 | 1.23 | 1.23 | 1.32 | 1.33 | 1.24 | 6.2% |
| 4 | 0.25 | 0.25 | 0.23 | 0.26 | 0.29 | 0.32 | 0.27 | 12.1% |
| 5 | 0.03 | 0.02 | 0.02 | 0.03 | 0.03 | 0.03 | 0.03 | 20.0% |

TABLE 9

| Positive Pool Dilution | Run 1 (CV) | Run 2 (CV) | Run 3 (CV) | Run 4 (CV) | Run 5 (CV) | Run 6 (CV) | Intra-run Avg CV |
|---|---|---|---|---|---|---|---|
| 1 | 5.3% | 3.9% | 2.5% | 4.9% | 4.0% | 6.3% | 4.5% |
| 2 | 0.2% | 5.2% | 1.0% | 8.2% | 4.3% | 2.0% | 3.5% |
| 3 | 6.3% | 10.3% | 3.0% | 4.6% | 3.5% | 7.2% | 5.8% |
| E 4 | 7.9% | 13.4% | 20.1% | 14.7% | 20.2% | 18.5% | 15.8% |
| 5 | 44.3% | 25.6% | 22.1% | 26.6% | 8.5% | 20.1% | 24.5% |

Clinical Sensitivity

One hundred twenty seven (127) serum and plasma samples from 31 people with COVID-19 infection as confirmed by RNA RT-PCR were tested in the assay. Samples from people positive for SARS-CoV-2 were broken into several categories based on the duration from the positive PCR test to sample collection. Cut-off for seropositivity was established based on the ROC analysis of the data with optimization for high specificity. The positive and negative percent agreement between the results obtained with the developed test and the RT-PCR results was calculated. Table 10 summarizes the data for all PCR positive samples.

TABLE 10

| Days from positive PCR test | First Serial Measurement | | Second Serial Measurement | | Third Serial Measurement | | Total PPA/Sensitivity (95% CI) |
|---|---|---|---|---|---|---|---|
| | Samples tested | Samples with pos results | Samples tested | Samples with pos results | Samples tested | Samples with pos results | |
| 0-7 | 30 | 13 | 22 | 15 | 16 | 13 | 60.3% (48.42-71.07) |
| 8-14 | 17 | 15 | 12 | 10 | 11 | 10 | 87.5% (73.89-94.54) |
| ≥15 | 10 | 10 | 5 | 5 | 4 | 4 | 100% (83.18-100.0) |

Note:
A positive PCR result confirms the presence of virus, but seroconversion to IgG reactivity follows a latency period of undetermined length. Therefore, samples collected early in the infection are expected to be non-reactive for anti-SARS-CoV-2 IgG.

Clinical Specificity

To support cross reactivity verification testing, 496 pre-pandemic serum and plasma samples (collected before December 2019) from apparently healthy individuals residing in the United States were tested. The tested population is expected to have high prevalence of vaccination against influenza, HBV, and *Haemophilus influenzae*. Cut-off for seropositivity was established to maximize specificity to >99%. A cut-off of 0.77 µg/mL resulted in 99.2% specificity (95% CI 97.95-99.69).

The invention claimed is:

1. A method for quantitatively detecting an antibody of a human to severe acute respiratory syndrome coronavirus 2 (BARS-Coir-2), which method comprises:
   a) contacting a sample from a human with SARS-CoV-2 S (spike) polypeptide, or a fragment thereof, to allow binding between an antibody to said SARS-CoV-2 S polypeptide, or a fragment thereof, if present in said sample, and said SARS-CoV-2 S polypeptide, or a fragment thereof;
   b) assessing a detectable signal due to binding between said antibody and said SARS-CoV-2 S polypeptide, or a fragment thereof; and
   c) comparing said detectable signal to a calibration data set generated using a calibrator antibody that specifically binds to said SARS-CoV-2 S polypeptide, or a fragment thereof, at multiple concentrations or levels to assess amount, concentration or level of said antibody in said sample, and
   wherein said calibrator antibody is a chimeric antibody, or a fragment thereof, that comprises a human constant region and a variable region component or a variable region of a non-human species, and
   wherein said calibration data set is generated using said calibrator antibody, or a fragment thereof, at concentrations or levels ranging from about 0.001 ng/mL to about 10,000 ng/mL.

2. The method of claim 1, wherein step a) comprises contacting a sample from a human with a fragment of SARS-CoV-2 S (spike) polypeptide.

3. The method of claim 2, wherein the fragment of SARS-CoV-2 S (spike) polypeptide comprises the extracellular domain or fragment of SARS-CoV-2 S (spike) polypeptide.

4. The method of claim 1, wherein step b) comprises contacting a first complex formed between an antibody of a human and a SARS-CoV-2 S polypeptide, or a fragment thereof, with a binder that binds to the antibody in the first complex, and the binder comprising a detectable label, to form a second complex comprising the antibody, the SARS-CoV-2 S polypeptide, or a fragment thereof, and the binder comprising the detectable label.

5. The method of claim 1, wherein step b) comprises:
   1) Contacting a first complex formed between an antibody of a human and a SARS-CoV-2 S polypeptide, or a fragment thereof, with a binder that binds to the antibody in the first complex, and the binder comprising a first member of a binding pair, to form a second complex comprising the antibody, the SARS-CoV-2 S polypeptide or a fragment thereof, and the binder comprising the first member; and
   2) contacting the second complex with a second member of the binding pair that comprises a detectable label and binds to the first member of the binding pair to form a third complex comprising the antibody, the SARS-CoV-2 S polypeptide or a fragment thereof, the binder comprising the detectable label and the first member of the binding pair, and the second member of the binding pair.

6. The method of claim 4, wherein further comprises applying the second complex comprising the SARS-CoV-2 S polypeptide or a fragment thereof, the antibody, and the binder comprising a detectable label to a surface of a solid support.

7. The method of claim 6, wherein step b) further comprises assessing a detectable signal from a single second complex or a single third complex in a femtoliter reaction well.

8. The method of claim 1, wherein the calibrator antibody comprises an intact chimeric antibody, or the calibrator antibody is a recombinant chimeric antibody, or a fragment thereof.

9. The method of claim 1, which is used to quantitatively detect a human antibody to SARS-CoV-2.

10. The method of claim 1, wherein the calibrator antibody comprises a monoclonal antibody, or a fragment thereof.

11. The method of claim 1, which is used to quantitatively detect a single antibody to SARS-CoV-2, or is used to quantitatively detect multiple antibodies to SARS-CoV-2.

12. The method of claim 2, wherein the fragment of SARS-CoV-2 S polypeptide comprises an amino acid sequence set forth in SEQ ID NO:1.

13. The method of claim 2, wherein the fragment of SARS-CoV-2 S polypeptide comprises a soluble trimeric version of the SARS-CoV-2 spike protein.

14. The method of claim 13, wherein the SARS-CoV-2 spike protein comprises the spike protein of SARS-CoV-2 187 isolate (GenBank: MN908947.3).

15. The method of claim 4, wherein the binder is a protein or a polypeptide binder.

16. The method of claim 15, wherein the binder is an antibody.

17. The method of claim 6, wherein the surface of the solid support comprises a solid surface, a planar surface, a porous surface, a surface of a microtiter plate, or a surface of a microfluidic device.

18. The method of claim 17, wherein the microtiter plate is a 96/384 well microtiter plate, or a microtiter plate comprising microwells.

19. The method of claim 17, wherein the microfluidic device comprises an array of femtoliter reaction wells and is configured to petition a single second complex in a femtoliter reaction well.

20. The method of claim 5, which further comprises applying the third complex comprising the antigen or a fragment thereof, the antibody, the binder comprising the detectable label and the first member of the binding pair, and the second member of the binding pair, to a surface of a solid support.

21. The method of claim 20, which comprises applying the third complex to the surface of a microfluidic device that comprises an array of femtoliter reaction wells and petitioning a single third complex in a femtoliter reaction well.

* * * * *

SEQUENCE LISTING

```
<160> NUMBER OF SEQ ID NOS: 1

<210> SEQ ID NO 1
<211> LENGTH: 1261
<212> TYPE: PRT
<213> ORGANISM: SARS-CoV-2
<220> FEATURE:
<221> NAME/KEY: MISC_FEATURE
<222> LOCATION: (1)..(1261)
<223> OTHER INFORMATION: a SARS-CoV-2 S (spike) fragment
      ([PRO_0000449646; Aa 13-1273; GenBank Accession No. P0DTC2])

<400> SEQUENCE: 1

Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60
```

```
Lys Arg Phe Asp Asn Pro Val Leu Pro Phe Asn Asp Gly Val Tyr Phe
 65                  70                  75                  80

Ala Ser Thr Glu Lys Ser Asn Ile Ile Arg Gly Trp Ile Phe Gly Thr
                 85                  90                  95

Thr Leu Asp Ser Lys Thr Gln Ser Leu Leu Ile Val Asn Asn Ala Thr
                100                 105                 110

Asn Val Val Ile Lys Val Cys Glu Phe Gln Phe Cys Asn Asp Pro Phe
                115                 120                 125

Leu Gly Val Tyr Tyr His Lys Asn Asn Lys Ser Trp Met Glu Ser Glu
            130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
                165                 170                 175

Leu Arg Glu Phe Val Phe Lys Asn Ile Asp Gly Tyr Phe Lys Ile Tyr
                180                 185                 190

Ser Lys His Thr Pro Ile Asn Leu Val Arg Asp Leu Pro Gln Gly Phe
            195                 200                 205

Ser Ala Leu Glu Pro Leu Val Asp Leu Pro Ile Gly Ile Asn Ile Thr
210                 215                 220

Arg Phe Gln Thr Leu Leu Ala Leu His Arg Ser Tyr Leu Thr Pro Gly
225                 230                 235                 240

Asp Ser Ser Ser Gly Trp Thr Ala Gly Ala Ala Tyr Tyr Val Gly
                245                 250                 255

Tyr Leu Gln Pro Arg Thr Phe Leu Leu Lys Tyr Asn Glu Asn Gly Thr
                260                 265                 270

Ile Thr Asp Ala Val Asp Cys Ala Leu Asp Pro Leu Ser Glu Thr Lys
            275                 280                 285

Cys Thr Leu Lys Ser Phe Thr Val Glu Lys Gly Ile Tyr Gln Thr Ser
290                 295                 300

Asn Phe Arg Val Gln Pro Thr Glu Ser Ile Val Arg Phe Pro Asn Ile
305                 310                 315                 320

Thr Asn Leu Cys Pro Phe Gly Glu Val Phe Asn Ala Thr Arg Phe Ala
                325                 330                 335

Ser Val Tyr Ala Trp Asn Arg Lys Arg Ile Ser Asn Cys Val Ala Asp
            340                 345                 350

Tyr Ser Val Leu Tyr Asn Ser Ala Ser Phe Ser Thr Phe Lys Cys Tyr
            355                 360                 365

Gly Val Ser Pro Thr Lys Leu Asn Asp Leu Cys Phe Thr Asn Val Tyr
            370                 375                 380

Ala Asp Ser Phe Val Ile Arg Gly Asp Glu Val Arg Gln Ile Ala Pro
385                 390                 395                 400

Gly Gln Thr Gly Lys Ile Ala Asp Tyr Asn Tyr Lys Leu Pro Asp Asp
                405                 410                 415

Phe Thr Gly Cys Val Ile Ala Trp Asn Ser Asn Asn Leu Asp Ser Lys
                420                 425                 430

Val Gly Gly Asn Tyr Asn Tyr Leu Tyr Arg Leu Phe Arg Lys Ser Asn
            435                 440                 445

Leu Lys Pro Phe Glu Arg Asp Ile Ser Thr Glu Ile Tyr Gln Ala Gly
            450                 455                 460

Ser Thr Pro Cys Asn Gly Val Glu Gly Phe Asn Cys Tyr Phe Pro Leu
465                 470                 475                 480
```

-continued

```
Gln Ser Tyr Gly Phe Gln Pro Thr Asn Gly Val Gly Tyr Gln Pro Tyr
                485                 490                 495

Arg Val Val Leu Ser Phe Glu Leu Leu His Ala Pro Ala Thr Val
            500                 505                 510

Cys Gly Pro Lys Lys Ser Thr Asn Leu Val Lys Asn Lys Cys Val Asn
            515                 520                 525

Phe Asn Phe Asn Gly Leu Thr Gly Thr Gly Val Leu Thr Glu Ser Asn
530                 535                 540

Lys Lys Phe Leu Pro Phe Gln Gln Phe Gly Arg Asp Ile Ala Asp Thr
545                 550                 555                 560

Thr Asp Ala Val Arg Asp Pro Gln Thr Leu Glu Ile Leu Asp Ile Thr
                565                 570                 575

Pro Cys Ser Phe Gly Val Ser Val Ile Thr Pro Gly Thr Asn Thr
            580                 585                 590

Ser Asn Gln Val Ala Val Leu Tyr Gln Asp Val Asn Cys Thr Glu Val
        595                 600                 605

Pro Val Ala Ile His Ala Asp Gln Leu Thr Pro Thr Trp Arg Val Tyr
        610                 615                 620

Ser Thr Gly Ser Asn Val Phe Gln Thr Arg Ala Gly Cys Leu Ile Gly
625                 630                 635                 640

Ala Glu His Val Asn Asn Ser Tyr Glu Cys Asp Ile Pro Ile Gly Ala
                645                 650                 655

Gly Ile Cys Ala Ser Tyr Gln Thr Gln Thr Asn Ser Pro Arg Arg Ala
            660                 665                 670

Arg Ser Val Ala Ser Gln Ser Ile Ile Ala Tyr Thr Met Ser Leu Gly
            675                 680                 685

Ala Glu Asn Ser Val Ala Tyr Ser Asn Asn Ser Ile Ala Ile Pro Thr
        690                 695                 700

Asn Phe Thr Ile Ser Val Thr Thr Glu Ile Leu Pro Val Ser Met Thr
705                 710                 715                 720

Lys Thr Ser Val Asp Cys Thr Met Tyr Ile Cys Gly Asp Ser Thr Glu
                725                 730                 735

Cys Ser Asn Leu Leu Leu Gln Tyr Gly Ser Phe Cys Thr Gln Leu Asn
            740                 745                 750

Arg Ala Leu Thr Gly Ile Ala Val Glu Gln Asp Lys Asn Thr Gln Glu
            755                 760                 765

Val Phe Ala Gln Val Lys Gln Ile Tyr Lys Thr Pro Pro Ile Lys Asp
        770                 775                 780

Phe Gly Gly Phe Asn Phe Ser Gln Ile Leu Pro Asp Pro Ser Lys Pro
785                 790                 795                 800

Ser Lys Arg Ser Phe Ile Glu Asp Leu Leu Phe Asn Lys Val Thr Leu
                805                 810                 815

Ala Asp Ala Gly Phe Ile Lys Gln Tyr Gly Asp Cys Leu Gly Asp Ile
            820                 825                 830

Ala Ala Arg Asp Leu Ile Cys Ala Gln Lys Phe Asn Gly Leu Thr Val
            835                 840                 845

Leu Pro Pro Leu Leu Thr Asp Glu Met Ile Ala Gln Tyr Thr Ser Ala
850                 855                 860

Leu Leu Ala Gly Thr Ile Thr Ser Gly Trp Thr Phe Gly Ala Gly Ala
865                 870                 875                 880

Ala Leu Gln Ile Pro Phe Ala Met Gln Met Ala Tyr Arg Phe Asn Gly
                885                 890                 895

Ile Gly Val Thr Gln Asn Val Leu Tyr Glu Asn Gln Lys Leu Ile Ala
```

-continued

```
                  900                 905                 910
Asn Gln Phe Asn Ser Ala Ile Gly Lys Ile Gln Asp Ser Leu Ser Ser
            915                 920                 925
Thr Ala Ser Ala Leu Gly Lys Leu Gln Asp Val Val Asn Gln Asn Ala
        930                 935                 940
Gln Ala Leu Asn Thr Leu Val Lys Gln Leu Ser Ser Asn Phe Gly Ala
945                 950                 955                 960
Ile Ser Ser Val Leu Asn Asp Ile Leu Ser Arg Leu Asp Lys Val Glu
                965                 970                 975
Ala Glu Val Gln Ile Asp Arg Leu Ile Thr Gly Arg Leu Gln Ser Leu
            980                 985                 990
Gln Thr Tyr Val Thr Gln Gln Leu Ile Arg Ala Ala Glu Ile Arg Ala
        995                 1000                1005
Ser Ala Asn Leu Ala Ala Thr Lys Met Ser Glu Cys Val Leu Gly
    1010                1015                1020
Gln Ser Lys Arg Val Asp Phe Cys Gly Lys Gly Tyr His Leu Met
    1025                1030                1035
Ser Phe Pro Gln Ser Ala Pro His Gly Val Val Phe Leu His Val
    1040                1045                1050
Thr Tyr Val Pro Ala Gln Glu Lys Asn Phe Thr Thr Ala Pro Ala
    1055                1060                1065
Ile Cys His Asp Gly Lys Ala His Phe Pro Arg Glu Gly Val Phe
    1070                1075                1080
Val Ser Asn Gly Thr His Trp Phe Val Thr Gln Arg Asn Phe Tyr
    1085                1090                1095
Glu Pro Gln Ile Ile Thr Thr Asp Asn Thr Phe Val Ser Gly Asn
    1100                1105                1110
Cys Asp Val Val Ile Gly Ile Val Asn Asn Thr Val Tyr Asp Pro
    1115                1120                1125
Leu Gln Pro Glu Leu Asp Ser Phe Lys Glu Glu Leu Asp Lys Tyr
    1130                1135                1140
Phe Lys Asn His Thr Ser Pro Asp Val Asp Leu Gly Asp Ile Ser
    1145                1150                1155
Gly Ile Asn Ala Ser Val Val Asn Ile Gln Lys Glu Ile Asp Arg
    1160                1165                1170
Leu Asn Glu Val Ala Lys Asn Leu Asn Glu Ser Leu Ile Asp Leu
    1175                1180                1185
Gln Glu Leu Gly Lys Tyr Glu Gln Tyr Ile Lys Trp Pro Trp Tyr
    1190                1195                1200
Ile Trp Leu Gly Phe Ile Ala Gly Leu Ile Ala Ile Val Met Val
    1205                1210                1215
Thr Ile Met Leu Cys Cys Met Thr Ser Cys Cys Ser Cys Leu Lys
    1220                1225                1230
Gly Cys Cys Ser Cys Gly Ser Cys Cys Lys Phe Asp Glu Asp Asp
    1235                1240                1245
Ser Glu Pro Val Leu Lys Gly Val Lys Leu His Tyr Thr
    1250                1255                1260
```